US012611190B2

(12) United States Patent
Ebata

(10) Patent No.: US 12,611,190 B2
(45) Date of Patent: Apr. 28, 2026

(54) ULTRASOUND DIAGNOSTIC APPARATUS AND CONTROL METHOD OF ULTRASOUND DIAGNOSTIC APPARATUS FOR MEASURING A VOLUME OF A BLADDER OF A SUBJECT

(71) Applicant: FUJIFILM Corporation, Tokyo (JP)

(72) Inventor: Tetsurou Ebata, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1093 days.

(21) Appl. No.: 17/684,612

(22) Filed: Mar. 2, 2022

(65) Prior Publication Data

US 2022/0183663 A1     Jun. 16, 2022

Related U.S. Application Data

(63) Continuation of application No. PCT/JP2020/032409, filed on Aug. 27, 2020.

(30) Foreign Application Priority Data

Sep. 18, 2019     (JP) ................................. 2019-169129

(51) Int. Cl.
*A61B 8/00*          (2006.01)
*A61B 8/08*          (2006.01)
*A61B 8/14*          (2006.01)

(52) U.S. Cl.
CPC .............. *A61B 8/5223* (2013.01); *A61B 8/08* (2013.01); *A61B 8/14* (2013.01); *A61B 8/4254* (2013.01); *A61B 8/467* (2013.01); *A61B 8/54* (2013.01)

(58) Field of Classification Search
CPC ................ A61B 8/4245; A61B 8/4254; A61B 8/4263; A61B 8/085; A61B 5/4887; A61B 8/5223
See application file for complete search history.

(56) References Cited

U.S. PATENT DOCUMENTS

| | | | | |
|---|---|---|---|---|
| 6,290,648 B1* | 9/2001 | Kamiyama | .......... | A61B 8/4245 |
| | | | | 600/443 |
| 2016/0007972 A1* | 1/2016 | Nishiura | .............. | A61B 8/5269 |
| | | | | 600/437 |

(Continued)

FOREIGN PATENT DOCUMENTS

| | | | |
|---|---|---|---|
| JP | 2003-204962 A | | 7/2003 |
| JP | 2013158348 A | * | 8/2013 |

(Continued)

OTHER PUBLICATIONS

JP-2013158348-A (Year: 2013).*

(Continued)

*Primary Examiner* — Nyrobi Celestine

(74) *Attorney, Agent, or Firm* — Studebaker Brackett PLLC

(57)          ABSTRACT

An ultrasound diagnostic apparatus (1) includes an ultrasound probe (21); an inclination angle sensor (13) that detects an inclination angle thereof; an image acquisition unit (5) that acquires an ultrasound image; a bladder extraction unit (8) that extracts a bladder region from the ultrasound image; a feature quantity calculation unit (9) that calculates a feature quantity of the bladder region; a first measurement unit (10) that measures a first maximum diameter and a second maximum diameter of the bladder region from the feature quantity; a manipulation assist unit (11) that assists a user in a slide manipulation of the ultrasound probe (21) such that a scanning section indicates the first maximum diameter and the second maximum diameter; a second measurement unit (14) that measures a third maximum diameter of the bladder region orthogonal to the scanning section on the basis of the ultrasound image and the inclination angle at the assisted position; and a bladder (Continued)

volume calculation unit (15) that calculates a volume of the bladder.

19 Claims, 24 Drawing Sheets

(56)                  References Cited

U.S. PATENT DOCUMENTS

| | | | |
|---|---|---|---|
| 2016/0367218 A1* | 12/2016 | Kim | A61B 8/4427 |
| 2017/0164924 A1* | 6/2017 | Urabe | A61B 8/5223 |
| 2020/0100765 A1* | 4/2020 | Imai | G06T 7/62 |
| 2020/0345324 A1 | 11/2020 | Matsumoto et al. | |
| 2021/0353261 A1* | 11/2021 | Ebata | A61B 8/085 |

FOREIGN PATENT DOCUMENTS

| | | |
|---|---|---|
| JP | 2017-109074 A | 6/2017 |
| WO | 2019/150715 A1 | 8/2019 |

OTHER PUBLICATIONS

International Search Report issued in PCT/JP2020/032409; mailed Nov. 2, 2020.

Written Opinion issued in PCT/JP2020/032409; mailed Nov. 2, 2020.

Y.Boykov and V.Kolmogorov, "An experimental comparison of min-cut/max-flow algorithm for energy minimization in vision", IEEE Transactions on Pattern Analysis and Machine Intelligence, 26, 9, pp. 1-34, Sep. 2004.

A.W.Michael Kass and D.Terzopoulos: "Snakes: Active contour models", Int.J.Computer Vision, 1, 4, pp. 321-331, 1988.

Krizhevsk et al.: ImageNet Classification with Deep Convolutional Neural Networks, Advances in Neural Information Processing Systems 25, pp. 1-9, 2012.

M.Sussman et al.: "A level set approach for computing solutions to incompressible two-phase flow", J.Comput.Phys, 114, 1, pp. 146-159, Mar. 1994.

* cited by examiner

TRANSDUCER ARRAY — 2

TRANSMISSION AND
RECEPTION CIRCUIT — 3

PULSER — 23

AMPLIFICATION
UNIT — 24

AD CONVERSION
UNIT — 25

BEAM FORMER — 26

IMAGE
GENERATION UNIT — 4

SIGNAL
PROCESSING UNIT — 27

DSC — 28

IMAGE
PROCESSING UNIT — 29

CURRENT  FIRST DIAMETER    ○   cm
         SECOND DIAMETER   ○   cm
MAXIMUM  FIRST DIAMETER    ○   cm
         SECOND DIAMETER   ○   cm
CURRENT / MAXIMUM
         FIRST DIAMETER    ○   %
         SECOND DIAMETER   ○   %

IT'S A SECTION INDICATING
THE MAXIMUM DIAMETER.
PLEASE INCLINE THE PROBE.

| | | |
|---|---|---|
| CURRENT AREA | O | cm² |
| MAXIMUM AREA | O | cm² |
| CURRENT / MAXIMUM | O | % |

CURRENT AREA    ◯ cm²
MAXIMUM AREA    ◯ cm²
CURRENT / MAXIMUM    ◯ %

AN

MAXIMUM FRAME

U2

ULTRASOUND DIAGNOSTIC APPARATUS AND CONTROL METHOD OF ULTRASOUND DIAGNOSTIC APPARATUS FOR MEASURING A VOLUME OF A BLADDER OF A SUBJECT

CROSS-REFERENCE TO RELATED APPLICATIONS

This application is a Continuation of PCT International Application No. PCT/JP2020/032409 filed on Aug. 27, 2020, which claims priority under 35 U.S.C. § 119(a) to Japanese Patent Application No. 2019-169129 filed on Sep. 18, 2019. Each of the above applications is hereby expressly incorporated by reference, in its entirety, into the present application.

BACKGROUND OF THE INVENTION

1. Field of the Invention

The present invention relates to an ultrasound diagnostic apparatus, and a control method of the ultrasound diagnostic apparatus which measure a urine amount in a bladder of a subject.

2. Description of the Related Art

In the related art, an ultrasound diagnostic apparatus has been known as an apparatus for obtaining an image of the inside of a subject. The ultrasound diagnostic apparatus generally comprises an ultrasound probe comprising a transducer array in which a plurality of ultrasonic transducers are arranged. In a state where the ultrasound probe is in contact with the body surface of the subject, an ultrasound beam is transmitted toward the inside of the subject from the transducer array and an ultrasound echo from the subject is received by the transducer array so that an electric signal corresponding to the ultrasound echo is acquired. Further, the ultrasound diagnostic apparatus electrically processes the obtained electric signal to generate an ultrasound image of the corresponding site of the subject.

By using the ultrasound diagnostic apparatus, the bladder of the subject can be observed, and the urine amount in the observed bladder can be measured. In general, since the urine amount in the bladder of the subject is substantially the same as the volume of the bladder of the subject, the volume of the bladder of the subject is measured as the urine amount. The volume of the bladder of the subject can be calculated, for example, by regarding the bladder as an ellipsoid and using the maximum diameter in a vertical direction, the maximum diameter in a lateral direction, and the maximum diameter in a depth direction of the bladder, but usually, in order to obtain the maximum diameters in the vertical direction, the lateral direction, and the depth direction of the bladder, it is necessary for the user to move the ultrasound probe, observe each of a tomographic image of the bladder in which the diameter in the vertical direction and the diameter in the lateral direction of the bladder are maximized, and a tomographic image of the bladder in which the diameter in the depth direction of the bladder is maximized, and manually measure the diameters of the bladder.

Therefore, an ultrasound diagnostic apparatus disclosed in JP2013-158348A has been developed in order to save the user's trouble of measuring the urine amount in the bladder of the subject. In the ultrasound diagnostic apparatus of JP2013-158348A, an inclination angle sensor that measures an inclination angle of the ultrasound probe is included in the ultrasound probe, and the diameter of the bladder in the depth direction is calculated on the basis of the inclination angle of the ultrasound probe measured while the ultrasound probe is inclined in a state where the ultrasound probe is in contact with the body surface of the subject and the position of the deepest portion of the bladder of the subject calculated from the ultrasound image at this time. While the ultrasound probe is inclined on the body surface of the subject, the diameter in the vertical direction and the diameter in the lateral direction of the bladder are also calculated, and the urine amount in the bladder is calculated on the basis of the obtained diameters in three directions.

SUMMARY OF THE INVENTION

Here, in a case where the urine amount in the bladder of the subject is measured using the ultrasound diagnostic apparatus of JP2013-158348A, it is necessary for the user to incline the ultrasound probe until the bladder is drawn in the ultrasound image in order to calculate the maximum diameter of the bladder in the depth direction. Further, in the ultrasound diagnostic apparatus of JP2013-158348A, it is necessary for the user to determine the position on the subject with which the ultrasound probe is to be in contact, for example, the ultrasound probe is placed at a position shifted from a portion directly above the center of the bladder of the subject in some cases. In this manner, in a case where the ultrasound probe is placed at a position shifted from a portion directly above the center of the bladder of the subject, it is necessary for the user to incline the ultrasound probe more than a case where the ultrasound probe is placed at a portion directly above the center of the bladder of the subject, and thus the ultrasound probe may be separated from the body surface of the subject, and the ultrasound probe may slip on the body surface of the subject so that the position of the ultrasound probe may be shifted. Thereby, there is a problem that the accuracy of measuring the urine amount in the bladder of the subject is lowered.

The present invention has been made in order to solve such a problem in the related art, and an object of the invention is to provide an ultrasound diagnostic apparatus and a control method of the ultrasound diagnostic apparatus which can measure the urine amount in the bladder of the subject with high accuracy.

In order to achieve the object, an ultrasound diagnostic apparatus according to an aspect of the present invention comprises an ultrasound probe that is brought into contact with a subject and performs scanning of an ultrasound beam on the subject; an inclination angle sensor that detects an inclination angle of the ultrasound probe; an image acquisition unit that acquires ultrasound images of a plurality of frames corresponding to a plurality of tomographic planes different from each other in the subject by using the ultrasound probe; a bladder extraction unit that extracts a bladder region from each of the ultrasound images of the plurality of frames; a feature quantity calculation unit that calculates a feature quantity relating to the bladder region extracted by the bladder extraction unit in each of the ultrasound images of the plurality of frames; a first measurement unit that measures a first maximum diameter and a second maximum diameter of the bladder region in two directions in a scanning section of the ultrasound probe on the basis of the feature quantity calculated by the feature quantity calculation unit from the ultrasound image acquired by the image acquisition unit while the ultrasound probe is being slid along a body surface of the subject; a manipulation assist unit that assists a user in a slide manipulation of the ultrasound probe to a target slide position along the body surface of the subject such that the scanning section of the ultrasound probe is a section indicating the first maximum diameter and the second maximum diameter; a second measurement unit that measures a third maximum diameter of the bladder region in a section orthogonal to the scanning section of the ultrasound probe on the basis of the ultrasound image acquired by the image acquisition unit while the inclination angle of the ultrasound probe is changed at the target slide position assisted by the manipulation assist unit and the inclination angle of the ultrasound probe detected by the inclination angle sensor; and a bladder volume calculation unit that calculates a volume of the bladder on the basis of the first maximum diameter and the second maximum diameter measured by the first measurement unit and the third maximum diameter measured by the second measurement unit.

The feature quantity calculation unit may calculate a first diameter and a second diameter of the bladder region in the two directions in the scanning section of the ultrasound probe, as the feature quantity.

Alternatively, the feature quantity calculation unit may also calculate a product of a first diameter and a second diameter of the bladder region in the two directions in the scanning section of the ultrasound probe, as the feature quantity.

Alternatively, the feature quantity calculation unit may also calculate an area of the bladder region in the scanning section of the ultrasound probe, as the feature quantity.

The first measurement unit may measure a first diameter and a second diameter in the two directions in the scanning section in which the feature quantity calculated by the feature quantity calculation unit is maximum, as the first maximum diameter and the second maximum diameter.

In this case, the first measurement unit may calculate a maximum feature quantity on the basis of the feature quantity calculated by the feature quantity calculation unit.

The ultrasound diagnostic apparatus may further comprise a monitor that displays the ultrasound image, and the manipulation assist unit may assist the user in the slide manipulation of the ultrasound probe to the target slide position by displaying assist information on the monitor.

In this case, the manipulation assist unit may display a ratio or difference between the feature quantity calculated by the feature quantity calculation unit and the maximum feature quantity measured by the first measurement unit, as the assist information on the monitor.

Further, in a case where the ratio of the feature quantity to the maximum feature quantity exceeds a ratio threshold value, or in a case where the difference between the maximum feature quantity and the feature quantity is equal to or less than a difference threshold value, the manipulation assist unit may display that the scanning section of the ultrasound probe is a section indicating the first maximum diameter and the second maximum diameter, on the monitor.

The manipulation assist unit may further display the ultrasound image representing the scanning section indicating the first maximum diameter and the second maximum diameter, as the assist information on the monitor.

The ultrasound diagnostic apparatus may further comprise a speaker, and the manipulation assist unit may assist the user in the slide manipulation of the ultrasound probe to the target slide position by emitting a sound from the speaker.

The ultrasound diagnostic apparatus may further comprise a lamp, and the manipulation assist unit may assist the user in the slide manipulation of the ultrasound probe to the target slide position by emitting light from the lamp.

Further, in a case where the feature quantity calculated by the feature quantity calculation unit in a state where the inclination angle of the ultrasound probe detected by the inclination angle sensor is zero is equal to or less than a predetermined ratio to the feature quantity calculated by the feature quantity calculation unit in a state where the ultrasound probe is placed at the target slide position and the inclination angle of the ultrasound probe detected by the inclination angle sensor is zero, the manipulation assist unit may assist the user in the slide manipulation of the ultrasound probe to the target slide position again.

The second measurement unit may measure the third maximum diameter on the basis of the ultrasound image acquired by the image acquisition unit and the inclination angle of the ultrasound probe while the inclination angle of the ultrasound probe is changed by inclining the ultrasound probe only in one side of the scanning section.

The ultrasound diagnostic apparatus may further comprise an apparatus control unit that controls the inclination angle sensor such that the inclination angle sensor is operated only in a case where the second measurement unit measures the third maximum diameter.

Alternatively, the ultrasound diagnostic apparatus may further comprise an apparatus main body that includes at least the bladder extraction unit, the feature quantity calculation unit, the first measurement unit, the manipulation assist unit, the second measurement unit, and the bladder volume calculation unit, and is connected to the ultrasound probe by wireless communication, and the ultrasound probe may comprise at least the inclination angle sensor, and a probe control unit that controls the inclination angle sensor such that the inclination angle sensor is operated only in a case where the second measurement unit measures the third maximum diameter.

The first measurement unit may measure the first maximum diameter and the second maximum diameter on the basis of the feature quantity calculated by the feature quantity calculation unit within a predetermined scanning time.

In this case, the ultrasound diagnostic apparatus may further comprise an input device for the user to perform an input operation, and in a case where an instruction to measure again the first maximum diameter and the second maximum diameter is input by the user through the input device, the first measurement unit may measure again the first maximum diameter and the second maximum diameter on the basis of the feature quantity calculated by the feature quantity calculation unit in the predetermined scanning time.

Here, it is preferable that the scanning time is adjusted on the basis of the user's input operation through the input device.

In a case where a difference between the feature quantities of the ultrasound images of the consecutive frames is greater than a predetermined value, the first measurement unit may measure the first maximum diameter and the second maximum diameter on the basis of the feature quantities of the ultrasound images of the frames other than the consecutive frames.

A control method of an ultrasound diagnostic apparatus according to another aspect of the present invention comprises performing scanning of an ultrasound beam on a subject by an ultrasound probe in contact with the subject; detecting an inclination angle of the ultrasound probe; acquiring ultrasound images of a plurality of frames corresponding to a plurality of tomographic planes different from each other in the subject by using the ultrasound probe;

extracting a bladder region from each of the ultrasound images of the plurality of frames; calculating a feature quantity relating to the bladder region which is extracted in each of the ultrasound images of the plurality of frames; measuring a first maximum diameter and a second maximum diameter of the bladder region in two directions in a scanning section of the ultrasound probe on the basis of the feature quantity calculated from the ultrasound image acquired while the ultrasound probe is being slid along a body surface of the subject; assisting a user in a slide manipulation of the ultrasound probe to a target slide position along the body surface of the subject such that the scanning section of the ultrasound probe is a section indicating the first maximum diameter and the second maximum diameter; measuring a third maximum diameter of the bladder region in a section orthogonal to the scanning section of the ultrasound probe on the basis of the ultrasound image acquired while the inclination angle of the ultrasound probe is changed at the assisted target slide position and the detected inclination angle of the ultrasound probe; and calculating a volume of the bladder on the basis of the measured first maximum diameter and second maximum diameter and the measured third maximum diameter.

According to the present invention, the ultrasound diagnostic apparatus comprises the inclination angle sensor that detects the inclination angle of the ultrasound probe; the bladder extraction unit that extracts the bladder region from each of the ultrasound images of the plurality of frames; the feature quantity calculation unit that calculates the feature quantity relating to the bladder region extracted by the bladder extraction unit in each of the ultrasound images of the plurality of frames; the first measurement unit that measures the first maximum diameter and the second maximum diameter of the bladder region in two directions in the scanning section of the ultrasound probe on the basis of the feature quantity calculated by the feature quantity calculation unit from the ultrasound image acquired by the image acquisition unit while the ultrasound probe is being slid along a body surface of the subject; the manipulation assist unit that assists the user in the slide manipulation of the ultrasound probe to the target slide position along the body surface of the subject such that the scanning section of the ultrasound probe is a section indicating the first maximum diameter and the second maximum diameter; the second measurement unit that measures the third maximum diameter of the bladder region in the section orthogonal to the scanning section of the ultrasound probe on the basis of the ultrasound image acquired by the image acquisition unit while the inclination angle of the ultrasound probe is changed at the target slide position assisted by the manipulation assist unit and the inclination angle of the ultrasound probe detected by the inclination angle sensor; and the bladder volume calculation unit that calculates the volume of the bladder on the basis of the first maximum diameter and the second maximum diameter measured by the first measurement unit and the third maximum diameter measured by the second measurement unit. Therefore, the urine amount in the bladder of the subject can be measured with high accuracy.

BRIEF DESCRIPTION OF THE DRAWINGS

FIG. 21 is a diagram schematically illustrating an example in which a ratio of a current area of the bladder to a maximum area of the bladder is displayed as the assist information in the first embodiment of the present invention.

FIG. 22 is a diagram schematically illustrating an example in which the ratio of the current area of the bladder to the maximum area of the bladder and the ultrasound image indicating the first maximum diameter and the second maximum diameter are displayed as the assist information in the first embodiment of the present invention.

DESCRIPTION OF THE PREFERRED EMBODIMENTS

Hereinafter, embodiments of the invention will be described with reference to the accompanying drawings.

The description of configuration requirements described below is given on the basis of the representative embodiment of the present invention, but the present invention is not limited to such an embodiment.

In the present specification, a numerical range represented using "to" means a range including the numerical values before and after "to" as a lower limit value and an upper limit value.

In the present specification, the terms "same" and "identical" include an error range generally allowed in the technical field.

First Embodiment

Figure 1:
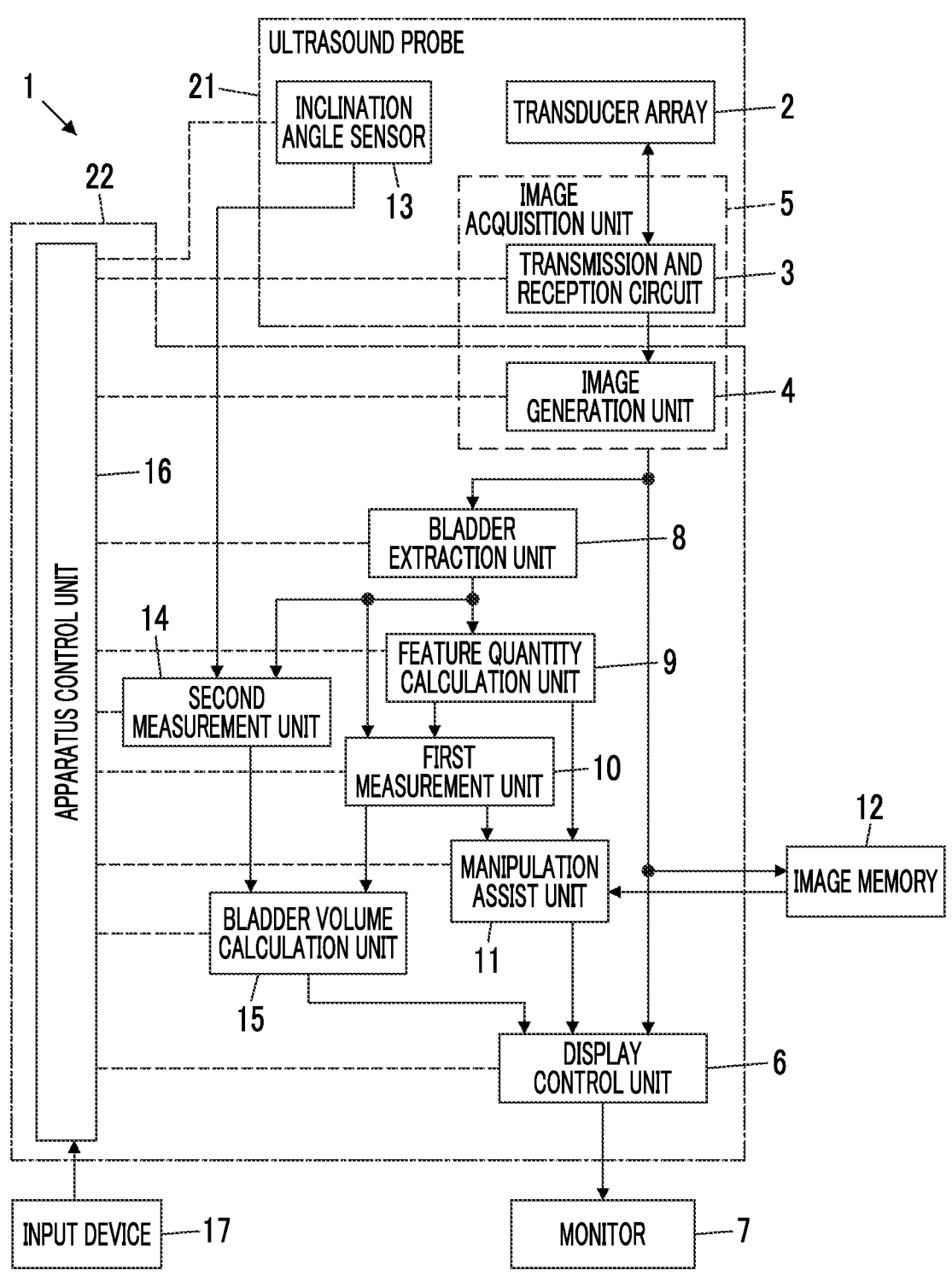
FIG. 1 is a block diagram illustrating a configuration of an ultrasound diagnostic apparatus according to a first embodiment of the present invention.

FIG. 1 illustrates a configuration of an ultrasound diagnostic apparatus 1 according to a first embodiment of the present invention. The ultrasound diagnostic apparatus 1 comprises a transducer array 2, and a transmission and reception circuit 3, an image generation unit 4, a display control unit 6, and a monitor 7 are sequentially connected to the transducer array 2. Here, the transmission and reception circuit 3 and the image generation unit 4 constitute an image acquisition unit 5. The transducer array 2 and the transmission and reception circuit 3 are included in an ultrasound probe 21. A bladder extraction unit 8 is connected to the image generation unit 4, and a feature quantity calculation unit 9 and a first measurement unit 10 are connected to the bladder extraction unit 8. Further, the first measurement unit 10 is connected to the feature quantity calculation unit 9. A manipulation assist unit 11 is connected to the feature quantity calculation unit 9 and the first measurement unit 10, and the display control unit 6 is connected to the manipulation assist unit 11. An image memory 12 is connected to the image generation unit 4, and the manipulation assist unit 11 is connected to the image memory 12. An inclination angle sensor 13 is included in the ultrasound probe 21. A second measurement unit 14 is connected to the bladder extraction unit 8 and the inclination angle sensor 13. A bladder volume calculation unit 15 is connected to the first measurement unit 10 and the second measurement unit 14, and the display control unit 6 is connected to the bladder volume calculation unit 15.

An apparatus control unit 16 is connected to the transmission and reception circuit 3, the image generation unit 4, the display control unit 6, the bladder extraction unit 8, the feature quantity calculation unit 9, the first measurement unit 10, the manipulation assist unit 11, the inclination angle sensor 13, the second measurement unit 14, and the bladder volume calculation unit 15. An input device 17 is connected to the apparatus control unit 16.

The transducer array 2, the transmission and reception circuit 3, and the inclination angle sensor 13 are included in the ultrasound probe 21. The image generation unit 4, the display control unit 6, the bladder extraction unit 8, the feature quantity calculation unit 9, the first measurement unit 10, the manipulation assist unit 11, the second measurement unit 14, the bladder volume calculation unit 15, and the apparatus control unit 16 constitute a processor 22 for the ultrasound diagnostic apparatus 1. The ultrasound diagnostic apparatus 1 comprises an apparatus main body (not illustrated) including the processor 22, and it is assumed that the apparatus main body and the ultrasound probe 21 are connected to each other by wired communication.

The transducer array 2 of the ultrasound probe 21 illustrated in FIG. 1 has a plurality of transducers arranged in a one-dimensional or two-dimensional manner. According to a drive signal supplied from the transmission and reception circuit 3, each of the transducers transmits an ultrasonic wave and receives an ultrasound echo from a subject to output a signal based on the ultrasound echo. For example, each transducer is configured by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

Figures 2, 3:
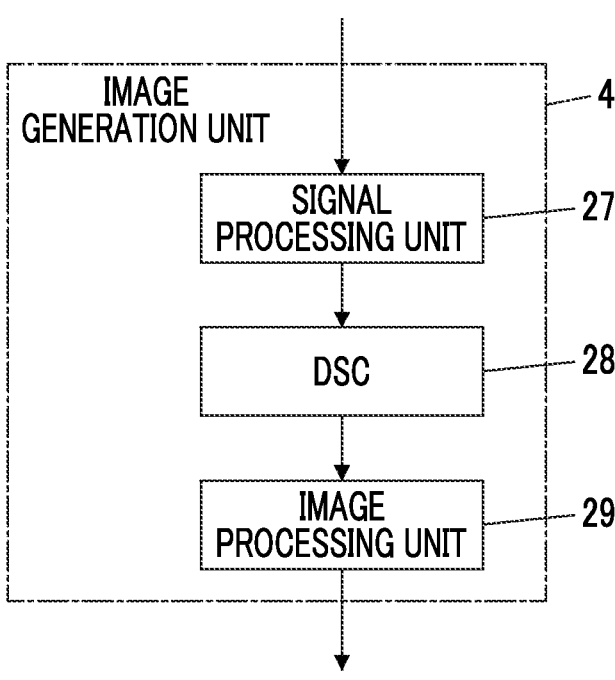
FIG. 2 is a block diagram illustrating an internal configuration of a transmission and reception circuit in the first embodiment of the present invention.
FIG. 3 is a block diagram illustrating an internal configuration of an image generation unit in the first embodiment of the present invention.

The transmission and reception circuit 3 causes the transducer array 2 to transmit the ultrasonic wave and generates a sound ray signal on the basis of a reception signal acquired by the transducer array 2, under the control of the apparatus control unit 16. As illustrated in FIG. 2, the transmission and reception circuit 3 has a pulser 23 connected to the transducer array 2, and an amplification unit 24, an analog digital (AD) conversion unit 25, and a beam former 26 that are sequentially connected in series from the transducer array 2.

The pulser 23 includes, for example, a plurality of pulse generators, and the pulser 23 adjusts the amount of delay of each drive signal so that ultrasonic waves transmitted from the plurality of transducers of the transducer array 2 form an ultrasound beam on the basis of a transmission delay pattern selected according to the control signal from the apparatus control unit 16, and supplies the obtained signals to the plurality of transducers. Thus, in a case where a pulsed or continuous-wave voltage is applied to the electrodes of the transducers of the transducer array 2, the piezoelectric body expands and contracts to generate pulsed or continuous-wave ultrasonic waves from each transducer. From the combined wave of these ultrasonic waves, an ultrasound beam is formed.

The transmitted ultrasound beam is reflected by a target, for example, a site of the subject, and propagates toward the transducer array 2 of the ultrasound probe 21. Each transducer constituting the transducer array 2 expands and contracts by receiving the ultrasound echo propagating toward the transducer array 2 in this manner, to generate the reception signal that is an electric signal, and outputs the reception signal to the amplification unit 24.

The amplification unit 24 amplifies the signals input from each transducer constituting the transducer array 2, and transmits the amplified signals to the AD conversion unit 25. The AD conversion unit 25 converts the signal transmitted from the amplification unit 24 into digital reception data, and transmits the reception data to the beam former 26. The beam former 26 performs so-called reception focusing processing in which addition is performed by giving delays to respective pieces of the reception data converted by the AD conversion unit 25 according to a sound speed distribution or a sound speed set on the basis of a reception delay pattern selected according to the control signal from the apparatus control unit 16. Through the reception focusing processing, a sound ray signal in which each piece of the reception data converted by the AD conversion unit 25 is phased and added and the focus of the ultrasound echo is narrowed is acquired.

As illustrated in FIG. 3, the image generation unit 4 has a configuration in which a signal processing unit 27, a digital scan converter (DSC) 28, and an image processing unit 29 are sequentially connected in series.

The signal processing unit 27 generates a B-mode image signal, which is tomographic image information regarding tissues inside the subject, by performing, on the sound ray signal generated by the beam former 26 of the transmission and reception circuit 3, correction of the attenuation due to the distance according to the depth of the reflection position of the ultrasonic wave and then performing envelope detection processing.

The DSC 28 converts (raster conversion) the B-mode image signal generated by the signal processing unit 27 into an image signal according to a normal television signal scanning method.

The image processing unit 29 performs various kinds of necessary image processing such as gradation processing on the B-mode image signal input from the DSC 28, and then outputs the B-mode image signal to the display control unit 6, the bladder extraction unit 8, and the second measurement unit 14. In the following, the B-mode image signal subjected to the image processing by the image processing unit 29 is simply referred to as an ultrasound image.

Figure 4:
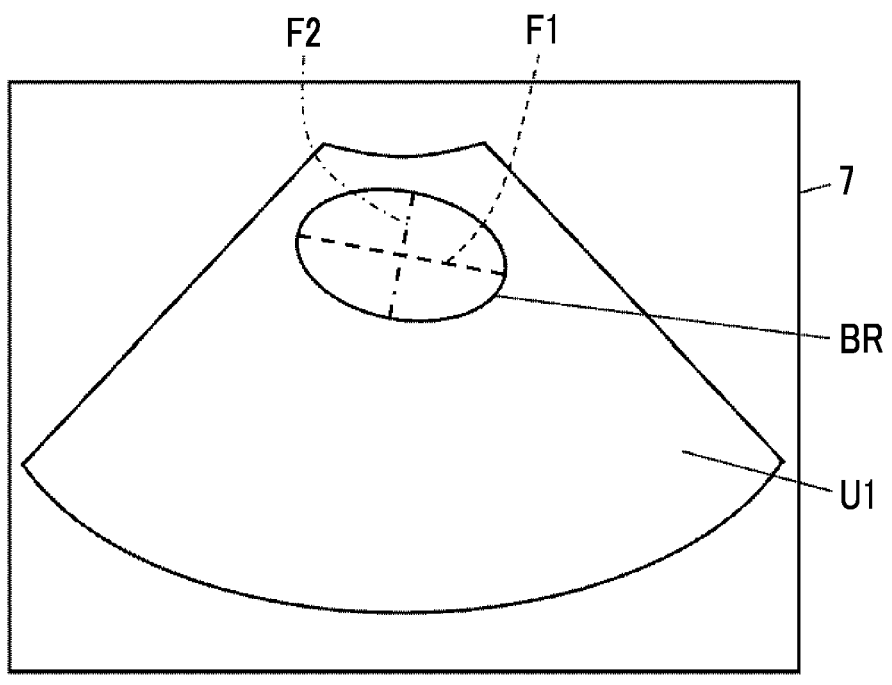
FIG. 4 is a diagram schematically illustrating an example of an ultrasound image including a bladder region in the first embodiment of the present invention.

The bladder extraction unit 8 extracts a bladder region BR from each of ultrasound images U1 of a plurality of frames generated by the image generation unit 4, as illustrated in FIG. 4, for example. The bladder extraction unit 8 can extract the bladder region BR in the ultrasound image U1 using a deep learning method disclosed in, for example, Krizhevsk et al.: ImageNet Classification with Deep Convolutional Neural Networks, Advances in Neural Information Processing Systems 25, pp. 1106-1114 (2012). Further, in order to extract the bladder region BR, the bladder extraction unit 8 can use known techniques such as graph cuts (Y. Boykov and V. Kolmogorov, "An experimental comparison of min-cut/max-flow algorithm for energy minimization in vision", IEEE Transactions on Pattern Analysis and Machine Intelligence, 26, 9, pp. 1123-1137, 2004.), Snakes (A. W. Michael Kass and D. Terzopoulos: "Snakes: Active contour models", Int. J. Computer Vision, 1, 4, pp. 321-331, 1988.), LevelSets (M. Sussman, P. Smereka and S. Osher: "A level set approach for computing solutions to incompressible two-phase flow", J. Comput. Phys, 114, 1, pp. 146-159, 1994), as other methods.

The feature quantity calculation unit 9 calculates a feature quantity relating to the extracted bladder region BR in each of the ultrasound images U1 of the plurality of frames from which the bladder region BR is extracted by the bladder extraction unit 8. The feature quantity calculation unit 9 can calculate, for example, the diameters of the extracted bladder region BR in two directions, the product of the diameters in two directions, the area of the bladder region BR, and the like as the feature quantity. Here, the diameters of the bladder region BR in two directions refer to a first diameter F1 as the maximum diameter of the bladder region BR and a second diameter F2 as the maximum diameter of the bladder region BR in a direction orthogonal to a direction along the first diameter F1, as illustrated in FIG. 4.

The first measurement unit 10 measures a first maximum diameter G1 and a second maximum diameter G2 in two directions, which are orthogonal to each other, of the bladder region BR in the scanning section of the ultrasound probe 21, on the basis of the feature quantity calculated by the feature quantity calculation unit 9 from the ultrasound image U1 acquired by the image acquisition unit 5 while sliding the ultrasound probe 21 along the body surface of the subject. For example, the first measurement unit 10 can calculate the maximum feature quantity on the basis of the feature quantity calculated by the feature quantity calculation unit 9 while the ultrasound probe 21 is slid along the body surface of the subject within a predetermined scanning time, select the ultrasound image U1 of the frame indicating the maximum feature quantity, and calculate the first diameter F1 and the second diameter F2 of the bladder region Br in two directions included in the selected ultrasound image U1 as the first maximum diameter G1 and the second maximum diameter G2, respectively.

Further, sliding the ultrasound probe 21 along the body surface of the subject means moving the ultrasound probe 21 along a certain direction while keeping the ultrasound probe 21 in contact with the body surface of the subject, and for example, includes not only moving the ultrasound probe 21 on the body surface of the subject while keeping the inclination angle of the ultrasound probe 21 substantially constant, but also inclining the ultrasound probe 21 after temporarily interrupting the movement of the ultrasound probe 21, and inclining the ultrasound probe 21 while moving the ultrasound probe 21. However, in order to improve the accuracy of calculating the maximum feature quantity, it is desirable to calculate the feature quantity of the bladder region BR in scanning sections parallel to each other, and it is desirable to move the ultrasound probe 21 on the body surface of the subject while keeping the inclination angle of the ultrasound probe 21 substantially constant.

The manipulation assist unit 11 assists the user in a slide manipulation of the ultrasound probe 21 to a target slide position along the body surface of the subject such that the scanning section of the ultrasound probe 21 is a section indicating the first maximum diameter G1 and the second maximum diameter G2. For example, the manipulation assist unit 11 can display assist information for assisting the user in the slide manipulation of the ultrasound probe 21, on the monitor 7. In this case, the manipulation assist unit 11 can display, as the assist information, the current feature quantity calculated by the feature quantity calculation unit 9, the maximum feature quantity calculated by the first measurement unit 10, and the ratio of the current feature quantity to the maximum feature quantity on the monitor 7, for example.

Figure 5:
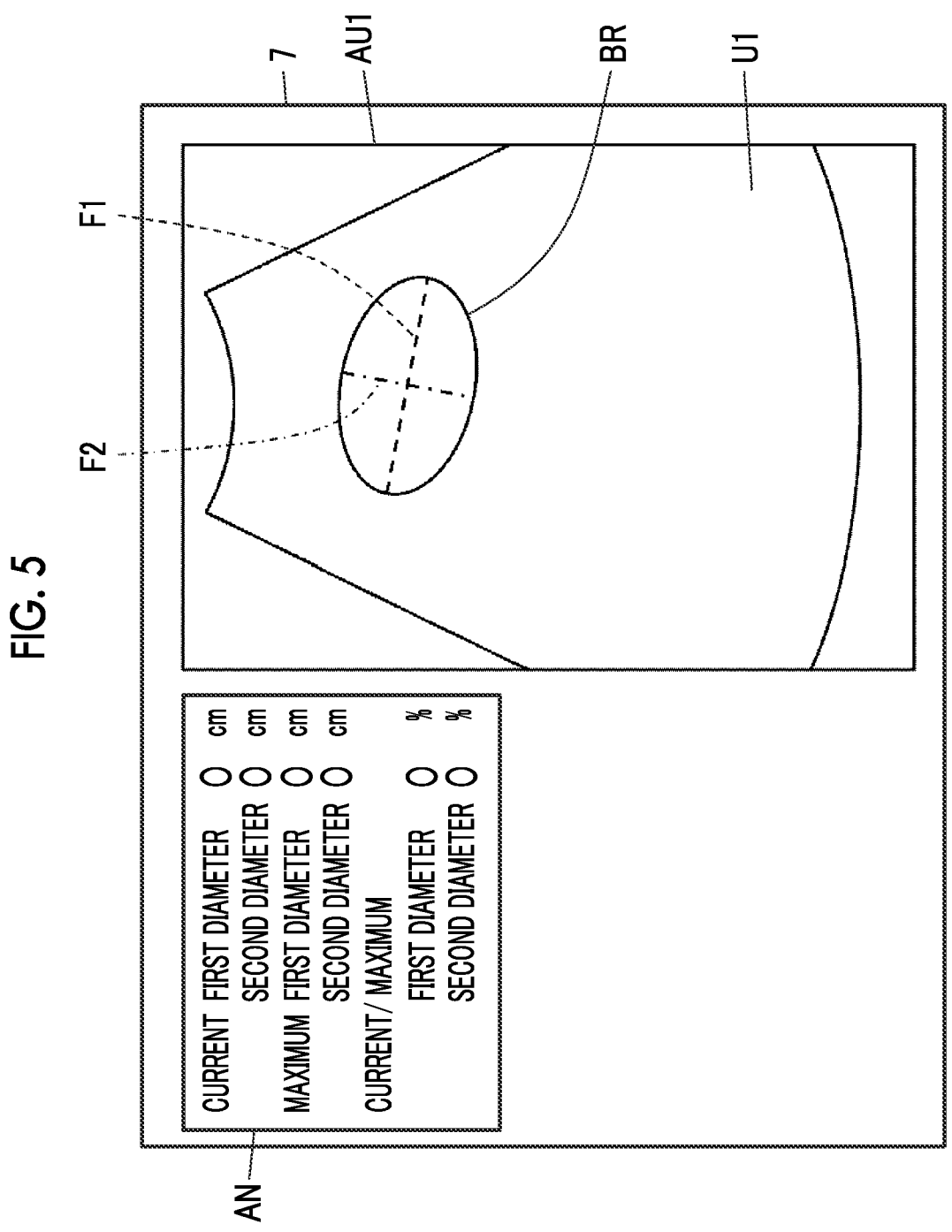
FIG. 5 is a diagram schematically illustrating an example of assist information displayed in the first embodiment of the present invention.

More specifically, the manipulation assist unit 11 can display, as the assist information, the current first diameter F1, the current second diameter F2, the first maximum diameter G1, the second maximum diameter G2, a ratio R1 of the first diameter F1 to the first maximum diameter G1, and a ratio R2 of the second diameter F2 to the second maximum diameter G2 on the monitor 7, as illustrated in FIG. 5, for example. In the example illustrated in FIG. 5, the monitor 7 has a current frame display region AU1 and a measurement value display region AN, and in the measurement value display region AN, a value of each of the current first diameter F1, the current second diameter F2, the first maximum diameter G1, the second maximum diameter G2, the ratio R1 of the first diameter F1 to the first maximum diameter G1, and the ratio R2 of the second diameter F2 to the second maximum diameter G2 is displayed as the assist information. Further, in the current frame display region AU1, the current ultrasound image U1 acquired by the image acquisition unit 5 is displayed.

In a case where the ratio of the current feature quantity calculated by the feature quantity calculation unit 9 to the maximum feature quantity calculated by the first measurement unit 10 exceeds a ratio threshold value such as 95 (%), the manipulation assist unit 11 can display the fact that the scanning section of the ultrasound probe 21 is the section indicating the first maximum diameter G1 and the second maximum diameter G2, on the monitor 7. For example, in a case where the ratio R1 of the first diameter F1 to the first maximum diameter G1 exceeds the ratio threshold value and the ratio R2 of the second diameter F2 to the second maximum diameter G2 exceeds the ratio threshold value, the manipulation assist unit 11 can display a message M1 indicating that the scanning section of the ultrasound probe 21 is the section indicating the first maximum diameter G1 and the second maximum diameter G2, on the monitor 7, as illustrated in FIG. 6.

Figure 6:
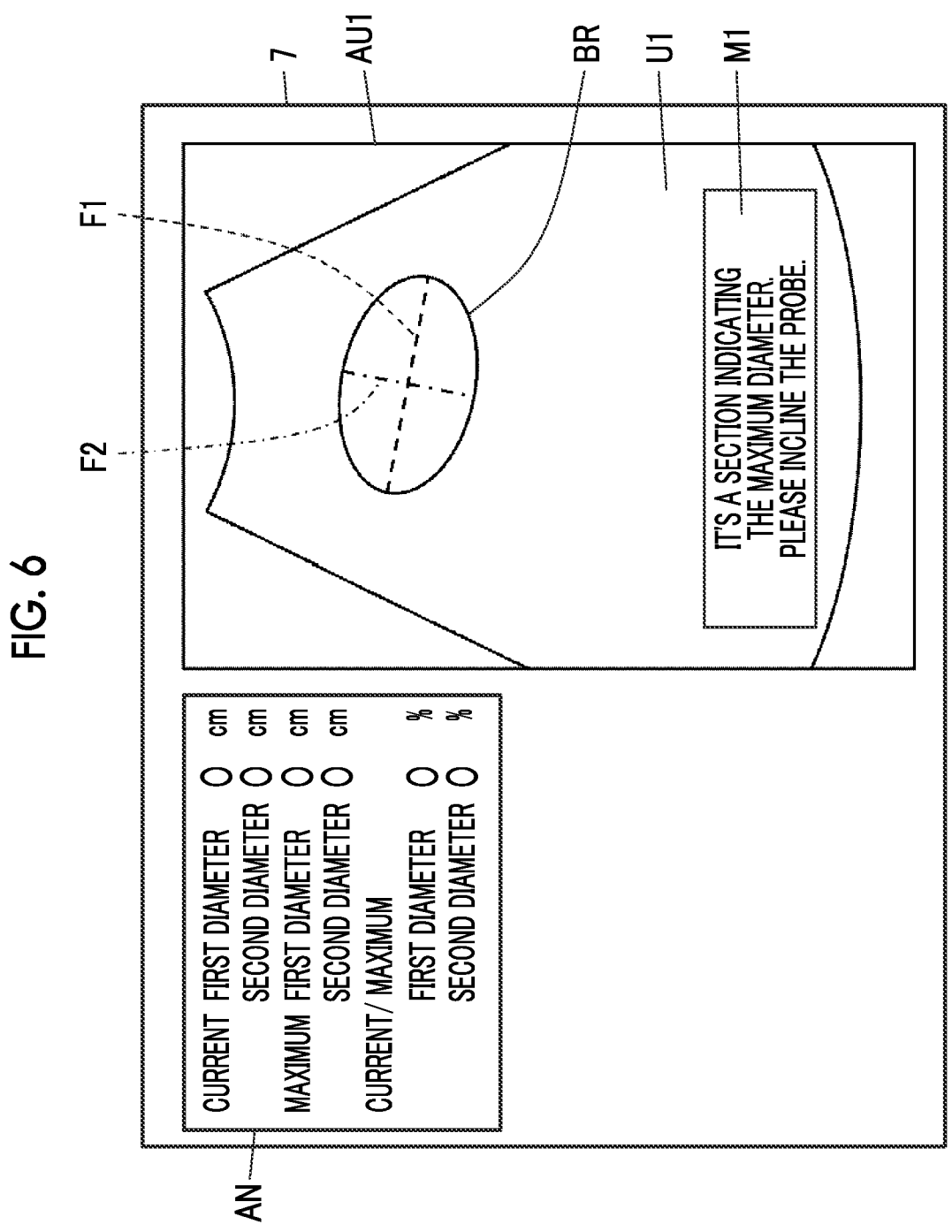
FIG. 6 is a diagram schematically illustrating an example of other assist information displayed in the first embodiment of the present invention.

In the example illustrated in FIG. 6, the message M1 "It's a section indicating the maximum diameter. Please incline the probe" is displayed on the monitor 7. The user performs the slide manipulation of the ultrasound probe 21 while checking such assist information, and places the ultrasound probe 21 at an appropriate slide position.

Figures 7, 8:
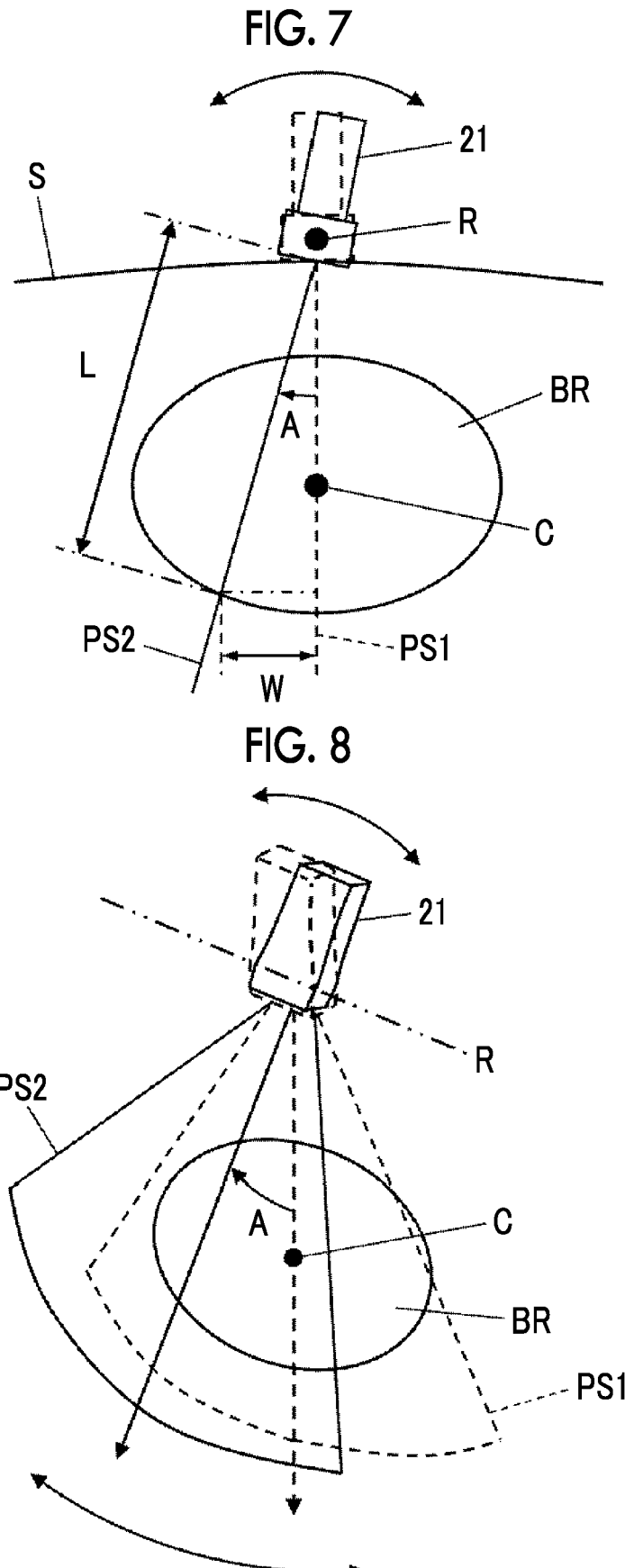
FIG. 7 is a diagram schematically illustrating an ultrasound probe in contact with a subject and a bladder of the subject positioned directly below the ultrasound probe in the first embodiment of the present invention.
FIG. 8 is a schematic diagram illustrating a form in which the ultrasound probe is inclined in the first embodiment of the present invention.

Here, for example, as illustrated in FIG. 7, the ultrasound images U1 of the plurality of frames can be acquired by the image acquisition unit 5 by a so-called swing method in which the ultrasound probe 21 is placed at the assisted target slide position and the ultrasound probe 21 is inclined around a rotation axis R parallel to the arrangement direction of the transducer array 2 while keeping the contact position of the ultrasound probe 21 with respect to a subject S constant, while changing an inclination angle A of the ultrasound probe 21. The arrangement direction of the transducer array 2 and the direction in which the rotation axis R extends are directions perpendicular to the paper surface in FIG. 7, and the ultrasound probe 21 is rotated around the rotation axis R so that a scanning section PS1 extending from the ultrasound probe 21 in the subject S is rotated around the rotation axis R.

The inclination angle A of the ultrasound probe 21 represents an angle at which the ultrasound probe 21 is inclined from a state where the normal direction of the transducer array 2 at the center of the transducer array 2 of the ultrasound probe 21 is directed in a direction perpendicular to the body surface of the subject S. That is, the inclination angle A is zero in the ultrasound probe 21 in a state where the normal direction of the transducer array 2 is directed in a direction perpendicular to the body surface of the subject S, and has a larger value as the ultrasound probe 21 is inclined from that state. In the examples illustrated in FIGS.

7 and 8, the inclination angle A is represented as a rotation angle between the scanning section PS1 in which the ultrasound probe 21 is directed in a direction perpendicular to the body surface of the subject S and a scanning section PS2 in a state where the ultrasound probe 21 is inclined.

The inclination angle sensor 13 measures the inclination angle A of the ultrasound probe 21 as illustrated in FIGS. 7 and 8. For example, the inclination angle sensor 13 includes a so-called gyro sensor, an acceleration sensor, a magnetic sensor, or the like, and converts an electric signal obtained from the gyro sensor, the acceleration sensor, the magnetic sensor, or the like into the inclination angle A of the ultrasound probe 21 using a well-known calculation method or the like.

Further, the inclination angle sensor 13 can assign a sign corresponding to the direction in which the ultrasound probe 21 is inclined, to the inclination angle A in order to distinguish the direction in which the ultrasound probe 21 is inclined. For example, with reference to the scanning section PS1 by the ultrasound probe 21 in a state where the inclination angle A is zero, in a case where the ultrasound probe 21 is inclined in one side of the scanning section PS1, the direction in which the ultrasound probe 21 is inclined can be set as a positive direction, and a positive sign can be assigned to the detected inclination angle A, and in a case where the ultrasound probe 21 is inclined in the other side of the scanning section PS1, the direction in which the ultrasound probe 21 is inclined can be set as a negative direction, and a negative sign can be assigned to the detected inclination angle A.

The second measurement unit 14 measures a third maximum diameter H of the bladder region BR in a section orthogonal to the scanning section PS1 by the ultrasound probe 21 in a state where the inclination angle A is zero, on the basis of the ultrasound image U1 acquired by the image acquisition unit 5 and the inclination angle A of the ultrasound probe 21 detected by the inclination angle sensor 13 while changing the inclination angle A of the ultrasound probe 21 at the target slide position assisted by the manipulation assist unit 11. Here, the third maximum diameter H of the bladder region BR refers to the maximum diameter of the bladder region BR in a direction orthogonal to both the direction along the first maximum diameter G1 and the direction along the second maximum diameter G2 of the bladder region BR.

Figures 9, 10:
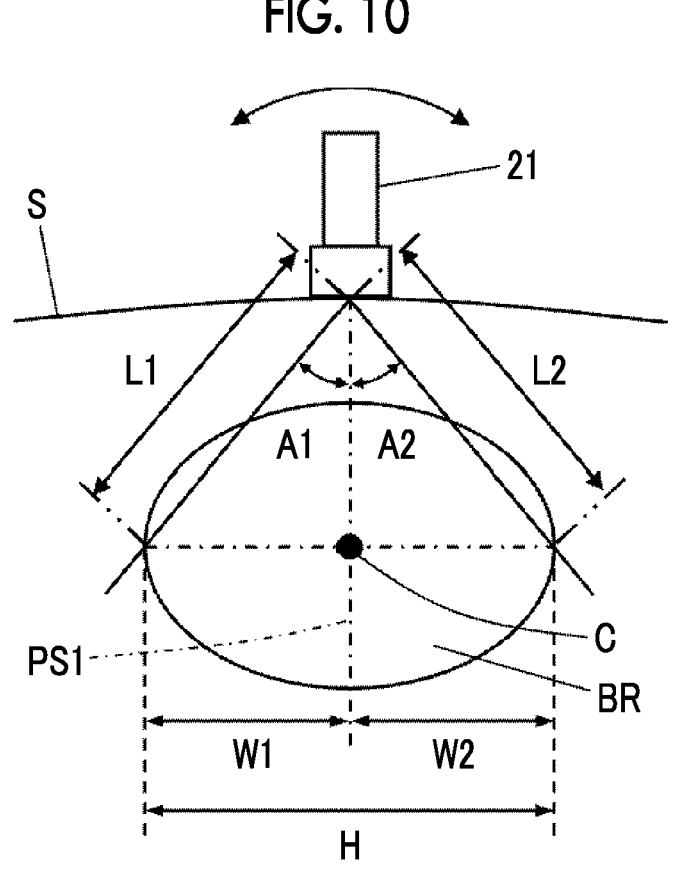
FIG. 9 is a diagram schematically illustrating a distance from a body surface of the subject to a deepest portion of the bladder region of the subject, which is measured in the first embodiment of the present invention.
FIG. 10 is a diagram schematically illustrating a third maximum diameter measured in the first embodiment of the present invention.

In a case of measuring the third maximum diameter H, the second measurement unit 14 can measure the distance L from the body surface of the subject S to the deepest portion of the bladder region BR extracted by the bladder extraction unit 8 as illustrated in FIG. 9, by analyzing the ultrasound image U1 acquired by the image acquisition unit 5, and calculate a third direction length W of the bladder region BR as the distance from the deepest portion of the bladder region BR to the scanning section PS1 in a state where the inclination angle A is zero, by a relational expression of $W = L \times |\sin(A)|$ using the calculated distance L and the inclination angle A of the ultrasound probe 21 detected by the inclination angle sensor 13. Here, $\sin(A)$ represents sine of the inclination angle A, and $|\sin(A)|$ represents the absolute value of $\sin(A)$. Further, the second measurement unit 14 can measure the shortest distance from the upper end portion of the ultrasound image U1 to the deepest portion of the bladder region BR in the direction along the scan line, as the distance L from the body surface of the subject S to the deepest portion of the bladder region BR.

The second measurement unit 14 can continue to calculate the third direction length W while the inclination angle A of the ultrasound probe 21 is changed, calculate each of a third direction length W1 that is maximum in a case where the ultrasound probe 21 is inclined in the positive direction and a third direction length W2 that is maximum in a case where the ultrasound probe 21 is inclined in the negative direction with reference to the scanning section PS1 as illustrated in FIG. 10, for example, and calculate the sum of the calculated third direction lengths W1 and W2 to calculate the third maximum diameter H.

In the example illustrated in FIG. 10, the third direction length W1 is calculated by a relational expression of $W1=L1\times|\sin(A1)|$ using a distance L1 from the body surface of the subject S to the deepest portion of the bladder region BR, which is measured in a case where the ultrasound probe 21 is inclined in the positive direction with reference to the scanning section PS1, and an inclination angle A1 of the ultrasound probe 21 in that case. Further, the third direction length W2 is calculated by a relational expression of $W2=L2\times|\sin(A2)|$ using a distance L2 from the body surface of the subject S to the deepest portion of the bladder region BR, which is measured in a case where the ultrasound probe 21 is inclined in the negative direction, and an inclination angle A2 of the ultrasound probe 21 in that case.

The second measurement unit 14 can determine whether or not an inclination manipulation of the ultrasound probe 21 by the user is completed, calculate the third direction lengths W1 and W2 in a case where it is determined that the inclination manipulation of the ultrasound probe 21 is completed, and calculate the sum of the third direction lengths W1 and W2 to calculate the third maximum diameter H. For example, as the inclination manipulation of the ultrasound probe 21, in a case where the ultrasound probe 21 is inclined in each of the positive direction and the negative direction until the bladder region BR is no longer drawn in the ultrasound image U1, the second measurement unit 14 can determined that the inclination manipulation of the ultrasound probe 21 by the user is completed in a case where it is detected that the inclination angle A detected by the inclination angle sensor 13 is changed in the order of zero, a positive maximum inclination angle, zero, a negative maximum inclination angle, and zero, or is changed in the order of zero, the negative maximum inclination angle, zero, the positive maximum inclination angle, and zero. Here, the inclination angle A of the ultrasound probe 21 when the user inclines the ultrasound probe 21 in the positive direction with reference to the scanning section PS1 and the bladder region BR is no longer drawn in the ultrasound image U1 is called the positive maximum inclination angle, and the inclination angle A of the ultrasound probe 21 when the user inclines the ultrasound probe 21 in the negative direction with reference to the scanning section PS1 and the bladder region BR is no longer drawn in the ultrasound image U1 is called the negative maximum inclination angle.

Figure 11:
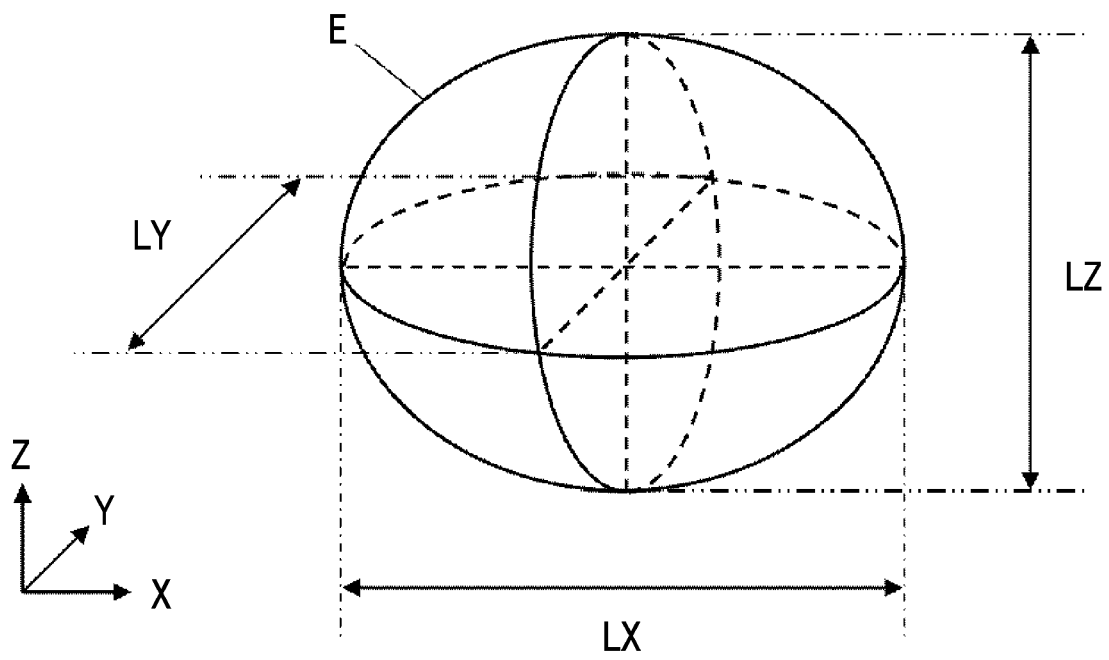
FIG. 11 is a diagram illustrating an example of an ellipsoid.

The bladder volume calculation unit 15 calculates the volume of the bladder of the subject S as the urine amount in the bladder of the subject S, on the basis of the first maximum diameter G1 and the second maximum diameter G2 measured by the first measurement unit 10 and the third maximum diameter H measured by the second measurement unit 14. Since the bladder generally has an approximately ellipsoidal shape, the bladder volume calculation unit 15 calculates the volume of the bladder as the volume of the ellipsoid. Here, as illustrated in FIG. 11, an ellipsoid E has a shape symmetrical with respect to the XY plane, the YZ plane, and the XZ plane, and it is known that the volume of the ellipsoid E is calculated by $(LX\times LY\times Z)\times\pi/6$, where the maximum diameter of the ellipsoid E in the X direction is LX, the maximum diameter of the ellipsoid E in the Y direction is LY, the maximum diameter of the ellipsoid E in the Z direction is LZ, and the ratio of the circumference of a circle to its diameter is $\pi$. Therefore, the bladder volume calculation unit 15 can calculate the volume of the bladder of the subject S by calculating (the first maximum diameter G1)×(the second maximum diameter G2)×(the third maximum diameter H)×$\pi$/6.

The image memory 12 stores the ultrasound image U1 acquired by the image acquisition unit 5. Here, as the image memory 12, recording media such as a flash memory, a hard disk drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), a server, or the like can be used.

The display control unit 6 performs predetermined processing on the ultrasound image U1 acquired by the image acquisition unit 5, the assist information by the manipulation assist unit 11, and the like to display the processed result on the monitor 7, under the control of the apparatus control unit 16.

The monitor 7 is for displaying the ultrasound image U1 acquired by the image acquisition unit 5, the assist information by the manipulation assist unit 11, and the like under the control of the display control unit 6, and includes a display device such as a liquid crystal display (LCD), or an organic electroluminescence (EL) display.

The input device 17 is for the user to perform an input operation, and can be configured to comprise a keyboard, a mouse, a trackball, a touchpad, a touch panel, and the like.

The apparatus control unit 16 controls each unit of the ultrasound diagnostic apparatus 1 on the basis of a control program and the like stored in advance.

The processor 22 having the image generation unit 4, the display control unit 6, the bladder extraction unit 8, the feature quantity calculation unit 9, the first measurement unit 10, the manipulation assist unit 11, the second measurement unit 14, the bladder volume calculation unit 15, and the apparatus control unit 16 is configured by a central processing unit (CPU) and a control program for causing the CPU to execute various kinds of processing, but the processor 22 may be configured by using a field programmable gate array (FPGA), a digital signal processor (DSP), an application specific integrated circuit (ASIC), a graphics processing unit (GPU), or other integrated circuits (IC) or may be configured by a combination thereof.

Further, the image generation unit 4, the display control unit 6, the bladder extraction unit 8, the feature quantity calculation unit 9, the first measurement unit 10, the manipulation assist unit 11, the second measurement unit 14, the bladder volume calculation unit 15, and the apparatus control unit 16 of the processor 22 can also be configured by being integrated partially or entirely into one CPU or the like.

In the following, the operation of the ultrasound diagnostic apparatus 1 of the first embodiment will be described in detail using the flowchart illustrated in FIG. 12.

First, in Step S1, the ultrasound image U1 is generated, and the generated ultrasound image U1 is displayed on the monitor 7. In this case, the ultrasound probe 21 is brought into contact with the body surface of the subject S by the user, an ultrasound beam is transmitted into the subject S from the plurality of transducers of the transducer array 2 according to the drive signal from the pulser 23 of the transmission and reception circuit 3, and the reception signal is output to the amplification unit 24 of the transmission and reception circuit 3 from each transducer which has received the ultrasound echo from the subject S. The reception signal is amplified in the amplification unit 24, is subjected to the AD conversion in the AD conversion unit 25, and is phased and added in the beam former 26, and thereby the sound ray signal is generated. The sound ray signal is subjected to the envelope detection processing by the signal processing unit 27 to be the B-mode image signal in the image generation unit 4, and is output to the display control unit 6 via the DSC 28 and the image processing unit 29, and the ultrasound image U1 is displayed on the monitor 7 under the control of the display control unit 6 as illustrated in FIG. 4.

Figure 13:
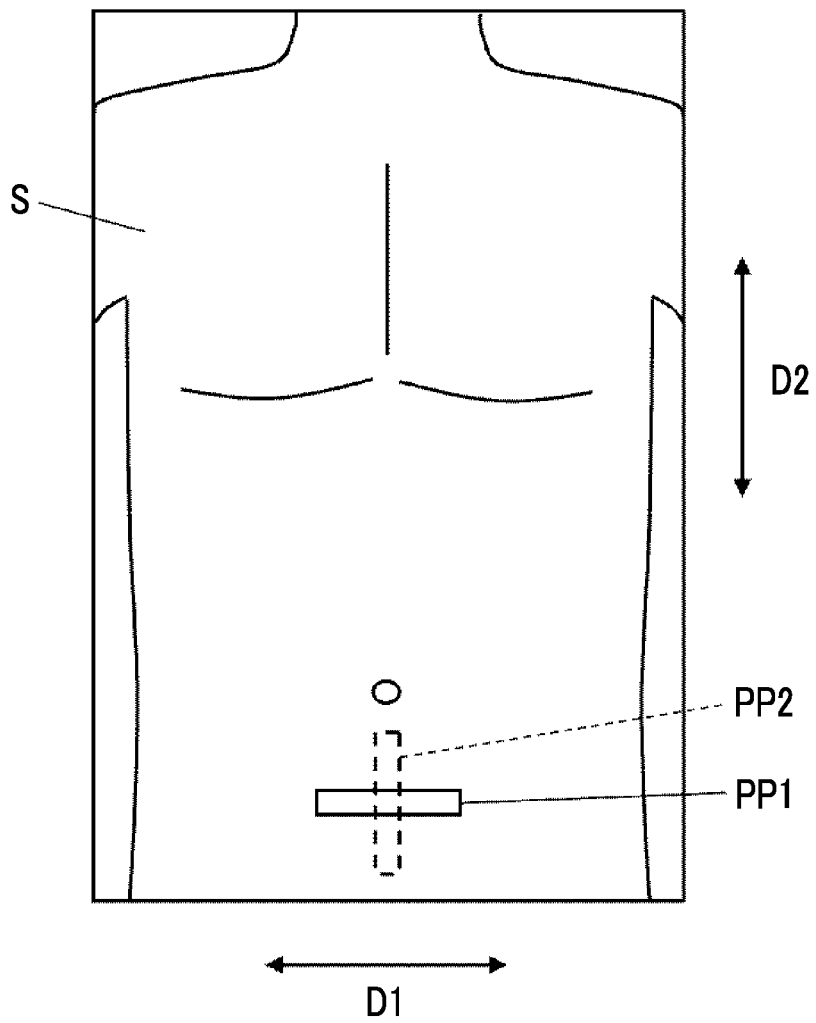
FIG. 13 is a diagram illustrating an example of a contact position of the ultrasound probe with respect to the subject in the first embodiment of the present invention.

In this case, for example, as illustrated in FIG. 13, in a case where three directions of a lateral direction D1 when facing the subject S from the front, a vertical direction D2 along a height direction of the subject S, and a depth direction (not illustrated) orthogonal to both the lateral direction D1 and the vertical direction D2 are regarded as one of the X direction, the Y direction, and the Z direction in the ellipsoid E, respectively, the user places the ultrasound probe 21 at any of a first contact position PP1 for observing a tomographic plane of the bladder along the lateral direction D1 of the subject S and a second contact position PP2 for observing a tomographic plane of the bladder along the vertical direction D2 of the subject S to capture the ultrasound image U1, and adjusts the position of the ultrasound probe 21 such that the bladder region BR is drawn in the ultrasound image U1.

Next, in Step S2, it is determined whether the measurement of the urine amount in the bladder of the subject S is started by the apparatus control unit 16. For example, in a case where an instruction to start the measurement of the urine amount is input by the user through the input device 17, the apparatus control unit 16 can determine that the measurement of the urine amount in the bladder of the subject S is started, and in a case where an instruction to start the measurement of the urine amount is not input, the apparatus control unit 16 can determine that the measurement of the urine amount in the bladder of the subject S is not started. For example, in a case where the user continues to adjust the position of the ultrasound probe 21 and the instruction to start the measurement of the urine amount is not input by the user through the input device 17, it is determined that the measurement of the urine amount in the bladder of the subject S is not started, the processing returns to Step S1, the ultrasound image U1 is acquired, and then the processing proceeds to Step S2. Further, for example, in a case where the user finishes adjusting the position of the ultrasound probe 21 and an instruction to start the measurement of the urine amount is input by the user through the input device 17, it is determined that the measurement of the urine amount in the bladder of the subject S is started, and the processing proceeds to Step S3.

Figure 14:
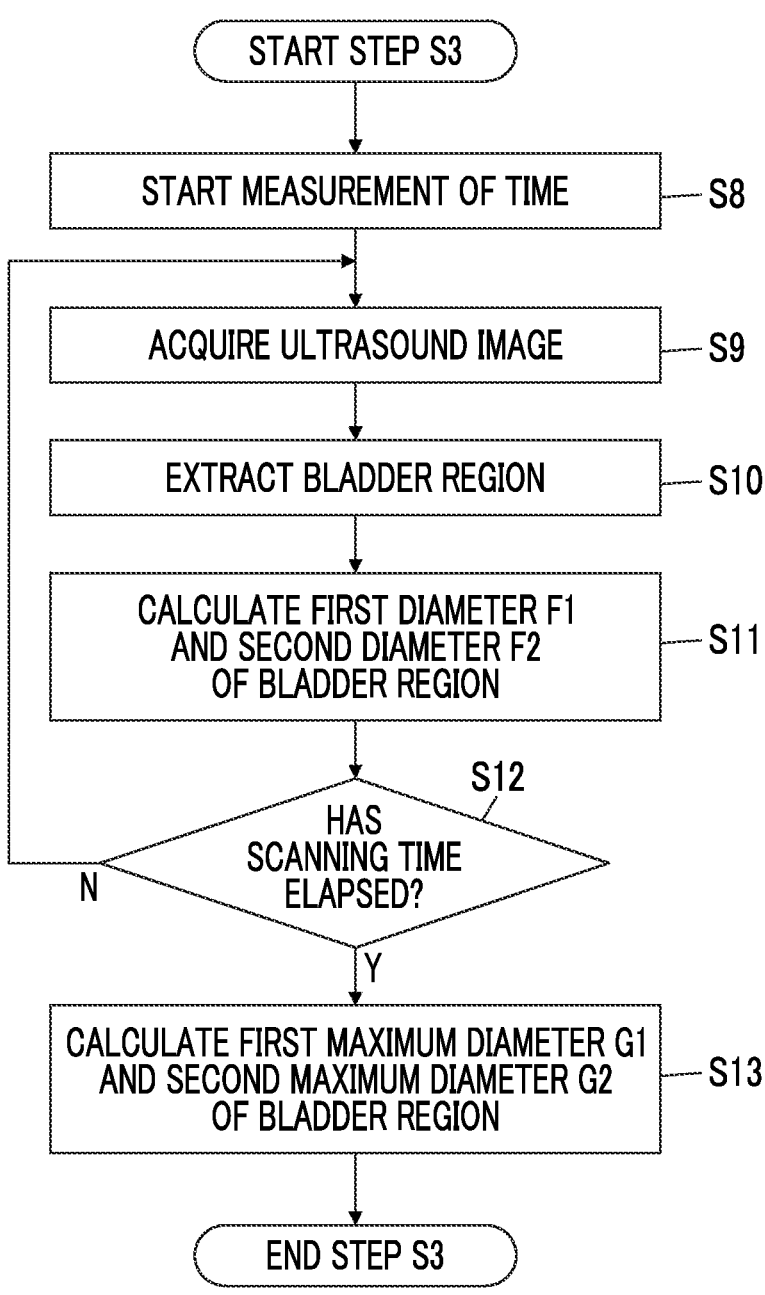
FIG. 14 is a flowchart illustrating an operation of calculating a first maximum diameter and a second maximum diameter of the bladder of the subject in the first embodiment of the present invention.

In Step S3, the first measurement unit 10 acquires the first maximum diameter G1 and the second maximum diameter G2 of the bladder region BR included in the ultrasound image U1 on the basis of the ultrasound image U1 acquired by the image acquisition unit 5 within the predetermined scanning time. The operation of the ultrasound diagnostic apparatus 1 in Step S3 will be described in detail using the flowchart illustrated in FIG. 14.

First, in Step S8, the apparatus control unit 16 starts the measurement of time. The time measured in this manner is used for determining whether or not a predetermined scanning time has elapsed, as will be described later.

Next, in Step S9, the ultrasound image U1 is acquired by the image acquisition unit 5. In this case, the user captures the ultrasound image U1 while performing the slide manipulation of the ultrasound probe 21.

In subsequent Step S10, the bladder extraction unit 8 extracts the bladder region BR included in the ultrasound image U1 acquired in Step S9. The bladder extraction unit 8 can extract the bladder region BR in the ultrasound image U1 using a deep learning method disclosed in, for example, Krizhevsk et al.: ImageNet Classification with Deep Convolutional Neural Networks, Advances in Neural Information Processing Systems 25, pp. 1106-1114 (2012). Further, in order to extract the bladder region BR, the bladder extraction unit 8 can use known techniques such as graph cuts (Y. Boykov and V. Kolmogorov, "An experimental comparison of min-cut/max-flow algorithm for energy minimization in vision", IEEE Transactions on Pattern Analysis and Machine Intelligence, 26, 9, pp. 1123-1137, 2004.), Snakes (A. W. Michael Kass and D. Terzopoulos: "Snakes: Active contour models", Int. J. Computer Vision, 1, 4, pp. 321-331, 1988.), LevelSets (M. Sussman, P. Smereka and S. Osher: "A level set approach for computing solutions to incompressible two-phase flow", J. Comput. Phys, 114, 1, pp. 146-159, 1994), as other methods.

In Step S11, the feature quantity calculation unit 9 calculates the feature quantity relating to the bladder region BR extracted in Step S9. Here, for the description, it is assumed that the feature quantity calculation unit 9 calculates the first diameter F1 and the second diameter F2 of the bladder region BR as the feature quantity. In this case, the feature quantity calculation unit 9 can calculate the maximum diameter of the bladder region BR in the ultrasound image U1 as the first diameter F1, and calculate the maximum diameter of the bladder region BR in a direction orthogonal to the direction along the first diameter F1 as the second diameter F2, as illustrated in FIG. 4, for example.

In Step S12, the apparatus control unit 16 determines whether or not the predetermined scanning time has elapsed by referring to the elapse time from the time point when the measurement of the time is started in Step S8. In a case where it is determined that the predetermined scanning time has not elapsed, the processing returns to Step S9, the ultrasound image U1 is acquired, the bladder region BR is extracted in Step S10, and the first diameter F1 and the second diameter F2 of the bladder region BR are calculated in Step S11. In this manner, until the predetermined scanning time elapses, the processing of Step S9 to Step S12 is repeated. In Step S12, in a case where it is determined that the predetermined scanning time has elapsed, the measurement of the time by the apparatus control unit 16 is ended, and the processing proceeds to Step S13.

In Step S13, the first measurement unit 10 selects a frame in which both the first diameter F1 and the second diameter F2 of the bladder region BR, which are calculated for the ultrasound images U1 of a plurality of frames obtained by repeating the processing of Step S9 to Step S12 within the predetermined scanning time, are maximum, and calculates the first diameter F1 and the second diameter F2 in the ultrasound image U1 of the frame as the first maximum diameter G1 and the second maximum diameter G2. In this manner, the processing of Step S3 is completed.

Figure 12:
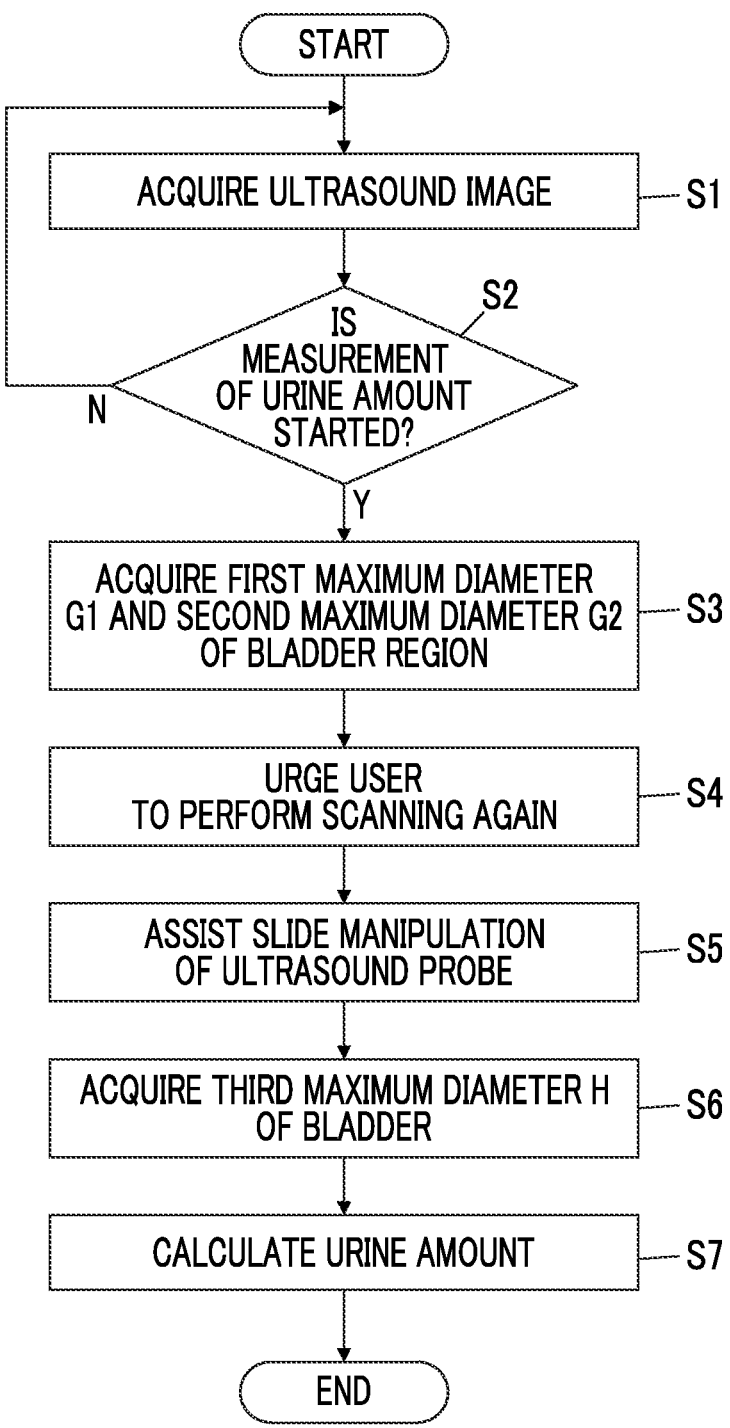
FIG. 12 is a flowchart illustrating an operation of the ultrasound diagnostic apparatus according to the first embodiment of the present invention.

As illustrated in FIG. 12, in a case where the processing of Step S3 is completed, the processing proceeds to Step S4.

Figure 15:
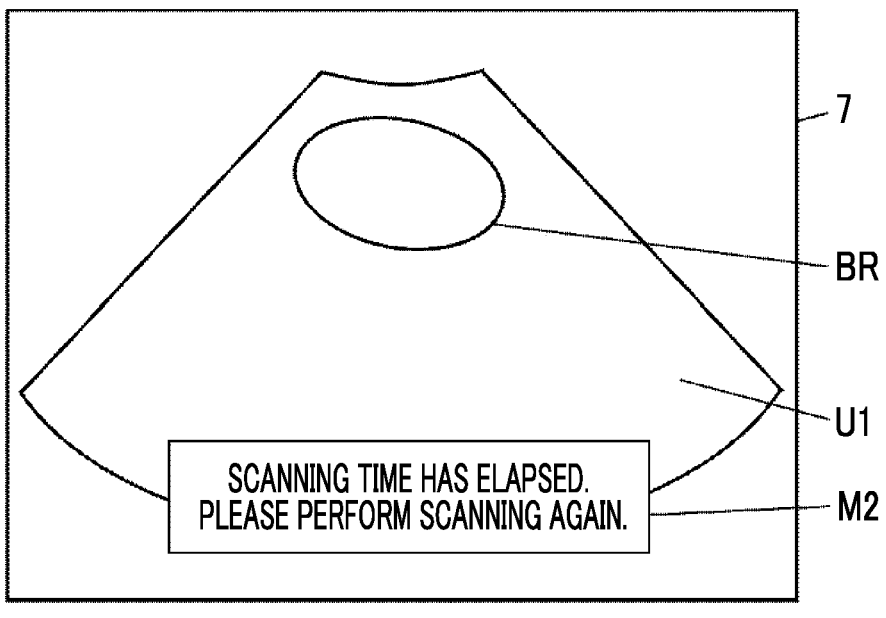
FIG. 15 is a diagram schematically illustrating an example of guide display in the first embodiment of the present invention.

In Step S4, a message M2 indicating that the predetermined scanning time has elapsed and urging the scanning by the ultrasound probe 21 again is displayed on the monitor 7 by the apparatus control unit 16 as illustrated in FIG. 15. In the example illustrated in FIG. 15, the message M2 "Scanning time has elapsed. Please perform scanning again" is displayed on the monitor 7. The user checks the message M2, and performs the slide manipulation of the ultrasound probe 21 again on the body surface of the subject S.

Figure 16:
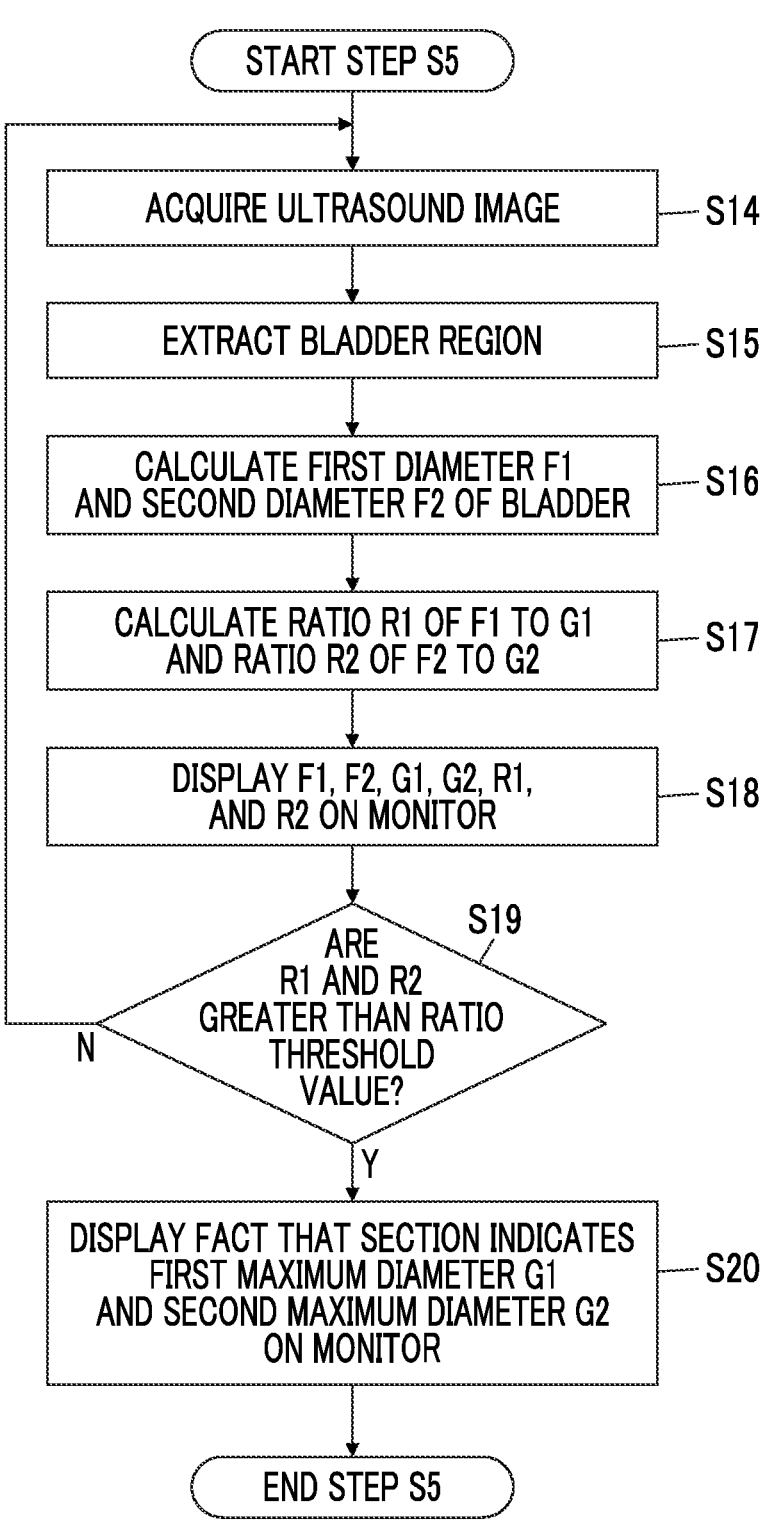
FIG. 16 is a flowchart illustrating an operation of assisting slide scanning of the ultrasound probe in the first embodiment of the present invention.

In subsequent Step S5, the manipulation assist unit 11 assists the user in the slide manipulation of the ultrasound probe 21 to the target slide position such that the scanning section of the ultrasound probe 21 is a section indicating the first maximum diameter G1 and the second maximum diameter G2. The operation of the ultrasound diagnostic apparatus 1 in Step S5 will be described in detail using the flowchart illustrated in FIG. 16.

First, in Step S14, the ultrasound image U1 is acquired by the image acquisition unit 5.

Next, in Step S15, the bladder region BR included in the ultrasound image U1 acquired in Step S14 is extracted by the bladder extraction unit 8.

In subsequent Step S16, as the feature quantity, the first diameter F1 and the second diameter F2 of the bladder region BR extracted in Step S15 are calculated by the feature quantity calculation unit 9.

In Step S17, the manipulation assist unit 11 calculates the ratio R1 of the first diameter F1 calculated in Step S16 to the first maximum diameter G1 calculated in Step S3 and the ratio R2 of the second diameter F2 calculated in Step S16 to the second maximum diameter G2 calculated in Step S3. For example, the manipulation assist unit 11 can calculate the ratios R1 and R2 as a percentage by setting R1=(F1/G1)× 100(%) and R2=(F2/G2)×100(%).

In Step S18, as illustrated in FIG. 5, the manipulation assist unit 11 displays, on the monitor 7, the first diameter F1 and the second diameter F2 calculated in Step S16, the first maximum diameter G1 and the second maximum diameter G2 calculated in Step S3, and the ratios R1 and R2 calculated in Step S17 as the assist information for assisting the user in the slide manipulation of the ultrasound probe 21. The user can easily adjust the position of the ultrasound probe 21 such that the ultrasound image U1 corresponding to the scanning section indicating the first maximum diameter G1 and the second maximum diameter G2 is acquired by performing the slide manipulation of the ultrasound probe 21 while checking the assist information displayed in this manner.

In Step S19, the manipulation assist unit 11 determines whether or not both the ratios R1 and R2 calculated in Step S17 are greater than the predetermined ratio threshold value. Here, in a case where it is determined that at least one of the ratio R1 or the ratio R2 calculated in Step S17 is equal to or less than the predetermined ratio threshold value, the processing proceeds to Step S14. The ultrasound image U1 is acquired in Step S14, the bladder region BR is extracted in Step S15, the first diameter F1 and the second diameter F2 of the bladder region BR are calculated in Step S16, the ratio R1 of the first diameter F1 to the first maximum diameter G1 and the ratio R2 of the second diameter F2 to the second maximum diameter G2 are calculated in Step S17, the first diameter F1, the second diameter F2, the first maximum diameter G1, the second maximum diameter G2, and the ratios R1 and R2 are displayed on the monitor 7 in Step S18, and the processing proceeds to Step S19. In this manner, until it is determined in Step S19 that both the ratios R1 and R2 are greater than the predetermined ratio threshold value, the processing of Step S14 to Step S19 is repeated.

In Step S19, in a case where it is determined that both the ratios R1 and R2 calculated in Step S17 are greater than the predetermined ratio threshold value, the processing proceeds to Step S20.

In Step S20, as illustrated in FIG. 6, the manipulation assist unit 11 displays the message M1 representing that the ultrasound probe 21 is placed at the target slide position where the ultrasound image U1 corresponding to the scanning section indicating the first maximum diameter G1 and the second maximum diameter G2 is acquired, on the monitor 7. In the example illustrated in FIG. 6, the message M1 "It's a section indicating the maximum diameter. Please incline the probe" is displayed on the monitor 7. The user can easily place the ultrasound probe 21 at the target slide position where the ultrasound image U1 corresponding to the scanning section indicating the first maximum diameter G1 and the second maximum diameter G2 is acquired, by checking such a message M1. In this manner, the processing of Step S5 is completed.

Figure 17:
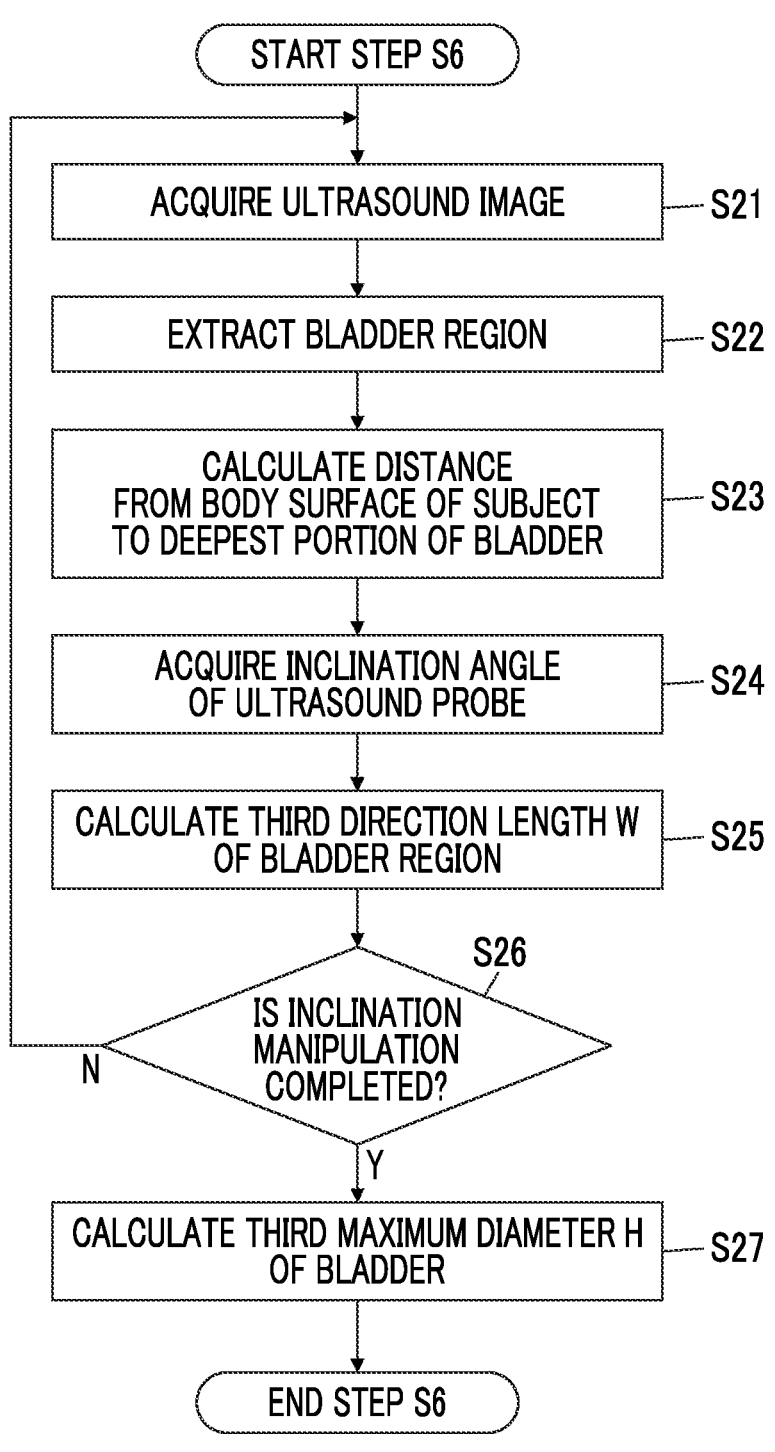
FIG. 17 is a flowchart illustrating an operation of calculating the third maximum diameter of the bladder of the subject in the first embodiment of the present invention.

In subsequent Step S6, the second measurement unit 14 acquires the third maximum diameter H of the bladder region BR. The operation of the ultrasound diagnostic apparatus 1 in Step S6 will be described in detail using the flowchart illustrated in FIG. 17.

First, the user inclines the ultrasound probe 21 such that the inclination angle A of the ultrasound probe 21 is changed at the assisted target slide position by checking the message M1 displayed on the monitor 7 in Step S5. For example, as illustrated in FIGS. 7 and 8, the user places the ultrasound probe 21 at the assisted target slide position, and inclines the ultrasound probe 21 around the rotation axis R parallel to the arrangement direction of the transducer array 2 while keeping the contact position of the ultrasound probe 21 with respect to the subject S constant. In this manner, the scanning section extending from the ultrasound probe 21 in the subject S is rotated around the rotation axis R. Here, as the inclination manipulation of the ultrasound probe 21 by the user, the ultrasound probe 21 is inclined in each of the positive direction and the negative direction until the bladder region BR is no longer drawn in the ultrasound image U1.

In this manner, the ultrasound image U1 is acquired by the image acquisition unit 5 in Step S21 while the ultrasound probe 21 is inclined by the user and the inclination angle A of the ultrasound probe 21 is changed.

Next, in Step S22, the bladder region BR included in the ultrasound image U1 acquired in Step S21 is extracted by the bladder extraction unit 8.

In subsequent Step S23, as illustrated in FIG. 9, the second measurement unit 14 measures the distance L from the body surface of the subject S to the deepest portion of the bladder region BR extracted in Step S22, by analyzing the ultrasound image U1 acquired in Step S21. For example, the second measurement unit 14 can measure the shortest distance from the upper end portion of the ultrasound image U1 to the deepest portion of the bladder region BR in the direction along the scan line, as the distance L from the body surface of the subject S to the deepest portion of the bladder region BR.

In Step S24, the inclination angle sensor 13 detects the inclination angle A of the ultrasound probe 21. The inclination angle sensor 13 can assign a sign corresponding to the direction in which the ultrasound probe 21 is inclined, to the inclination angle A in order to distinguish the direction in which the ultrasound probe 21 is inclined. For example, with reference to the scanning section PS1 in a state where the inclination angle A is zero, in a case where the ultrasound probe 21 is inclined in the positive direction, a positive sign can be assigned to the detected inclination angle A, and in a case where the ultrasound probe 21 is inclined in the negative direction, a negative sign can be assigned to the detected inclination angle A.

In Step S25, the second measurement unit 14 calculates the third direction length W of the bladder region BR as illustrated in FIG. 7. In this case, the second measurement unit 14 can calculate the third direction length W of the bladder region BR as the distance from the deepest portion of the bladder region BR to the scanning section PS1 in a state where the inclination angle A is zero, by the relational expression of $W=L \times |\sin(A)|$ using the distance L from the body surface of the subject S calculated in Step S23 and the inclination angle A of the ultrasound probe 21 detected in Step S24.

In Step S26, the second measurement unit 14 determines whether or not the inclination manipulation of the ultrasound probe 21 by the user is completed. For example, in a case where it is detected that the inclination angle A detected by the inclination angle sensor 13 is changed in the order of zero, the positive maximum inclination angle, zero, the negative maximum inclination angle, and zero, or is changed in the order of zero, the negative maximum inclination angle, zero, the positive maximum inclination angle, and zero, the second measurement unit 14 can determine that the inclination manipulation of the ultrasound probe 21 by the user is completed.

In a case where it is determined in Step S26 that the inclination manipulation of the ultrasound probe 21 by the user is not completed, the processing returns to Step S21. The ultrasound image U1 is acquired in Step S21, the bladder region BR included in the ultrasound image U1 is extracted in Step S22, the distance L from the body surface of the subject S to the deepest portion of the bladder region BR is calculated in Step S23, the inclination angle A of the ultrasound probe 21 is acquired in Step S24, and the third direction length W of the bladder region BR is calculated in Step S25. In this manner, until it is determined in Step S26 that the inclination manipulation of the ultrasound probe 21 is completed, the processing of Step S21 to Step S25 is repeated, and the third direction length W of the bladder region BR is calculated for the ultrasound images U1 of plurality of frames.

In a case where it is determined in Step S26 that the inclination manipulation of the ultrasound probe 21 by the user is completed, the processing proceeds to Step S27.

In Step S27, the second measurement unit 14 calculates the third maximum diameter H of the bladder region BR on the basis of the third direction length W calculated in Step S25 for the ultrasound images U1 of the plurality of frames. For example, as illustrated in FIG. 10, the second measurement unit 14 can calculate the third direction length W1 that is maximum in a case where the ultrasound probe 21 is inclined in the positive direction and the third direction length W2 that is maximum in a case where the ultrasound probe 21 is inclined in the negative direction with reference to the scanning section PS1 in which the inclination angle A of the ultrasound probe 21 is zero, and calculate the sum of the calculated third direction lengths W1 and W2 to calculate the third maximum diameter H.

Here, for example, when the ultrasound probe 21 is to be inclined, in a case where the position at which the ultrasound probe 21 is placed is apart from a portion directly above the center C of the bladder, since the ultrasound probe 21 is inclined until the inclination angle A of the ultrasound probe 21 is the positive maximum inclination angle or the negative maximum inclination angle, the user may have to significantly incline the ultrasound probe 21. In this case, by significantly inclining the ultrasound probe 21, the ultrasound probe 21 may be separated from the body surface of the subject S, and the ultrasound probe 21 may slip on the body surface of the subject S so that the ultrasound probe 21 may be shifted from the assisted target slide position, which may cause the accuracy of measuring the third maximum diameter H to be lowered.

The target slide position assisted by the manipulation assist unit 11 in Step S5 is a position near the portion directly above the center C of the bladder of the subject S, and the ultrasound probe 21 is not inclined more than necessary when the third maximum diameter H is measured. Therefore, it is suppressed that the ultrasound probe 21 is separated from the body surface of the subject S, and that the slide position of the ultrasound probe 21 is shifted, and thus the accuracy of measuring the third maximum diameter H is improved.

Figures 18, 19:
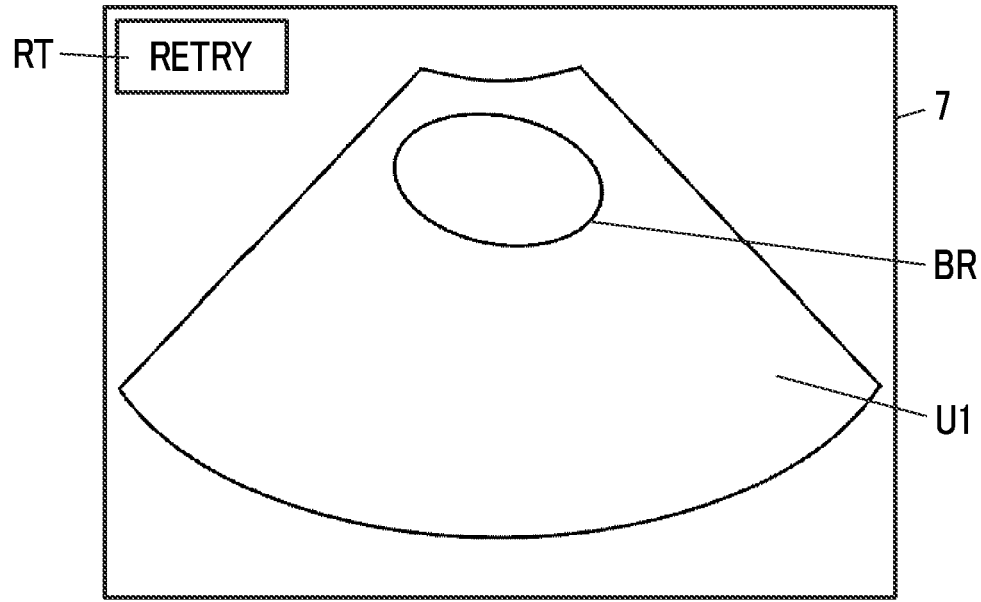
FIG. 18 is a diagram schematically illustrating an example in which a urine amount in the bladder of the subject is displayed on a monitor in the first embodiment of the present invention.
FIG. 19 is a diagram illustrating an example of a retry button in the first embodiment of the present invention.

In subsequent Step S7, the bladder volume calculation unit 15 calculates the volume of the bladder of the subject S as the urine amount in the bladder of the subject S on the basis of the first maximum diameter G1 and the second maximum diameter G2 of the bladder region BR acquired in Step S3 and the third maximum diameter H of the bladder region BR acquired in Step S6. More specifically, the bladder volume calculation unit 15 can calculate the volume of the bladder of the subject S by calculating (the first maximum diameter G1)×(the second maximum diameter G2)×(the third maximum diameter H)×$\pi/6$. Further, the bladder volume calculation unit 15 displays the calculated urine amount J in the bladder of the subject S on the monitor 7, as illustrated in FIG. 18, for example.

In this manner, the operation of the ultrasound diagnostic apparatus 1 measuring the urine amount J in the bladder of the subject S is completed.

From the above, with the ultrasound diagnostic apparatus 1 according to the first embodiment of the present invention, since the manipulation assist unit 11 assist the user in the slide manipulation of the ultrasound probe 21 to the target slide position such that the scanning section of the ultrasound probe 21 is a section indicating the first maximum diameter G1 and the second maximum diameter G2, and the third maximum diameter H of the bladder region BR is measured on the basis of the inclination angle A of the ultrasound probe 21 and the ultrasound image U1 acquired while changing the inclination angle A of the ultrasound probe 21 at the target slide position assisted by the manipulation assist unit 11, the third maximum diameter H is measured in a state where the ultrasound probe 21 is placed at a position near the portion directly above the center C of the bladder of the subject S. In this case, it is suppressed that the ultrasound probe 21 is separated from the body surface of the subject S, and that the slide position of the ultrasound probe 21 is shifted, and thus the urine amount J in the bladder of the subject S can be measured with high accuracy.

With the ultrasound diagnostic apparatus 1 according to the first embodiment of the present invention, since the urine amount J in the bladder of the subject S can be automatically and accurately measured only by performing the slide manipulation and the inclination manipulation of the ultrasound probe 21, it is possible to save the user's trouble in measuring the urine amount, and even a user with a low skill level can easily measure the urine amount J in the bladder of the subject S.

By using the ultrasound diagnostic apparatus 1, the user can measure the urine amount J only by, for example, manipulating the ultrasound probe 21 with one hand, and therefore, it is also possible to improve the work efficiency of the user in the ultrasound diagnosis, such as performing other work by the other hand not operating the ultrasound probe 21.

The beam former 26 that performs so-called reception focusing processing is included in the transmission and reception circuit 3, but can be included in the image generation unit 4, for example. Also in this case, similarly to the case where the beam former 26 is included in the transmission and reception circuit 3, the ultrasound image U1 is generated by the image generation unit 4.

The image generation unit 4 is included in the processor 22, but may be included in the ultrasound probe 21.

It has been described that the apparatus control unit 16 starts the measurement of time in Step S8, and determines whether or not the predetermined scanning time has elapsed in Step S12, but for example, the apparatus control unit 16 can display the elapse time from the start of the measurement of time in Step S8 to the current time point and the predetermined scanning time on the monitor 7. The apparatus control unit 16 can display the remaining time until the predetermined scanning time on the monitor 7, for example. The apparatus control unit 16 can also display images such as a bar graph and a circle graph representing the elapse time from the start of the measurement of time in Step S8 to the current time point or the remaining time until the predetermined scanning time on the monitor 7.

The predetermined scanning time can be set by the user's input operation through the input device 17, for example. For example, by setting the predetermined scanning time for each ultrasound diagnostic apparatus 1 used, it is possible to set the scanning time according to the location such as a hospital, and a medical department where the ultrasound diagnostic apparatus 1 is used.

For example, the scanning time can be set for each user who uses the ultrasound diagnostic apparatus 1. For example, a plurality of pieces of user identification information are stored for identifying the user, and the predetermined scanning time can be set for each of the plurality of pieces of the stored user identification information. In this case, for example, in a case where the user inputs the user identification information corresponding to him/her through the input device 17, the determination in Step S12 is performed by using the scanning time set for the user identification information. It is assumed that a user with a high skill level obtains the ultrasound image U1 indicating the first maximum diameter G1 and the second maximum diameter G2 within a short scanning time, but it is assumed that a user with a low skill level takes a lot of time to obtain the ultrasound image U1 indicating the first maximum diameter G1 and the second maximum diameter G2. Therefore, for example, even a user with a low skill level can measure the urine amount J with high accuracy by setting a longer scanning time as the skill level of the user is lower.

Further, the first measurement unit 10 can newly measure the first maximum diameter G1 and the second maximum diameter G2 of the bladder region BR by inputting the user's instruction through the input device 17 while measuring the first maximum diameter G1 and the second maximum diameter G2 of the bladder region BR in Step S3. More specifically, in a case where an instruction to measure again the first maximum diameter G1 and the second maximum diameter G2 is input by the user through the input device 17, the apparatus control unit 16 newly starts the measurement of time, and the first measurement unit 10 can measure again the first maximum diameter G1 and the second maximum diameter G2 on the basis of the feature quantity calculated by the feature quantity calculation unit 9 within the predetermined scanning time.

For example, as illustrated in FIG. 19, a retry button RT can be displayed on the monitor 7, and the instruction to measure again the first maximum diameter G1 and the second maximum diameter G2 can be input by the user pressing the retry button RT through the input device 17. In a case where the retry button RT is pressed by the user, the processing returns to Step S8, the measurement of time by the apparatus control unit 16 is started again, and the first maximum diameter G1 and the second maximum diameter G2 are measured again. In this manner, for example, in a case where the bladder region BR is not clearly drawn in the ultrasound image U1 or the like, the first maximum diameter G1 and the second maximum diameter G2 can be measured again, and therefore, the urine amount J can be measured with high accuracy.

Further, the predetermined scanning time can also be set according to the number of times the instruction to measure again the first maximum diameter G1 and the second maximum diameter G2 is input by the user through the input device 17. For example, in the first time of the urine amount measurement, the scanning time can be automatically set such that the scanning time is longer each time the instruction to measure again the first maximum diameter G1 and the second maximum diameter G2 is input. Further, the scanning time can also be set for each piece of the user identification information according to the frequency of inputting the instruction to measure again the first maximum diameter G1 and the second maximum diameter G2 per time of the urine amount measurement.

For example, in a state where the user identification information is input through the input device 17, in a case where the instruction to measure again the first maximum diameter G1 and the second maximum diameter G2 is repeatedly input a plurality of times during one time of the urine amount measurement, the scanning time is automatically set such that the scanning time is longer as the number of times the instruction to measure again the first maximum diameter G1 and the second maximum diameter G2 is input, and the set scanning time is stored in association with the input user identification information.

In this manner, the scanning time is set according to the number of times the instruction to measure again the first maximum diameter G1 and the second maximum diameter G2 is input, and thereby the measurement of the urine amount J can be performed in accordance with the skill level of the user who uses the ultrasound diagnostic apparatus 1.

It has been described that, as the assist information, the current first diameter F1 and second diameter F2, the first maximum diameter G1, the second maximum diameter G2, and the ratios R1 and R2 are displayed on the monitor 7 illustrated in FIGS. 5 and 6, but among these, only the current first diameter F1 and second diameter F2, the first maximum diameter G1, and the second maximum diameter G2 can be displayed on the monitor 7. Further, only the current first diameter F1 and second diameter F2, and the ratios R1 and R2 can be displayed on the monitor 7. Even in such a case, the user can easily place the ultrasound probe 21 at the target slide position where the ultrasound image U1 indicating the first maximum diameter G1 and the second maximum diameter G2 is acquired, by checking the assist information displayed on the monitor 7.

The manipulation assist unit 11 can display other assist information on the monitor 7 in addition to the current first diameter F1 and second diameter F2, the first maximum diameter G1, the second maximum diameter G2, the ratios R1 and R2, and the message M1 representing that the ultrasound probe 21 is placed at the target slide position where the ultrasound image U1 corresponding to the scanning section indicating the first maximum diameter G1 and the second maximum diameter G2 is acquired. For example, the manipulation assist unit 11 can also display, as the assist information, a measurement line representing the first diameter F1 and the second diameter F2 and a so-called caliper by superimposing the measurement line and caliper on the bladder region BR in the ultrasound image U1. Here, the caliper is positioned at both ends of the measurement line corresponding to the first diameter F1 and the second diameter F2, and indicates which two points on the contour of the bladder region BR are measured when the first diameter F1 and the second diameter F2 are measured.

Figure 20:
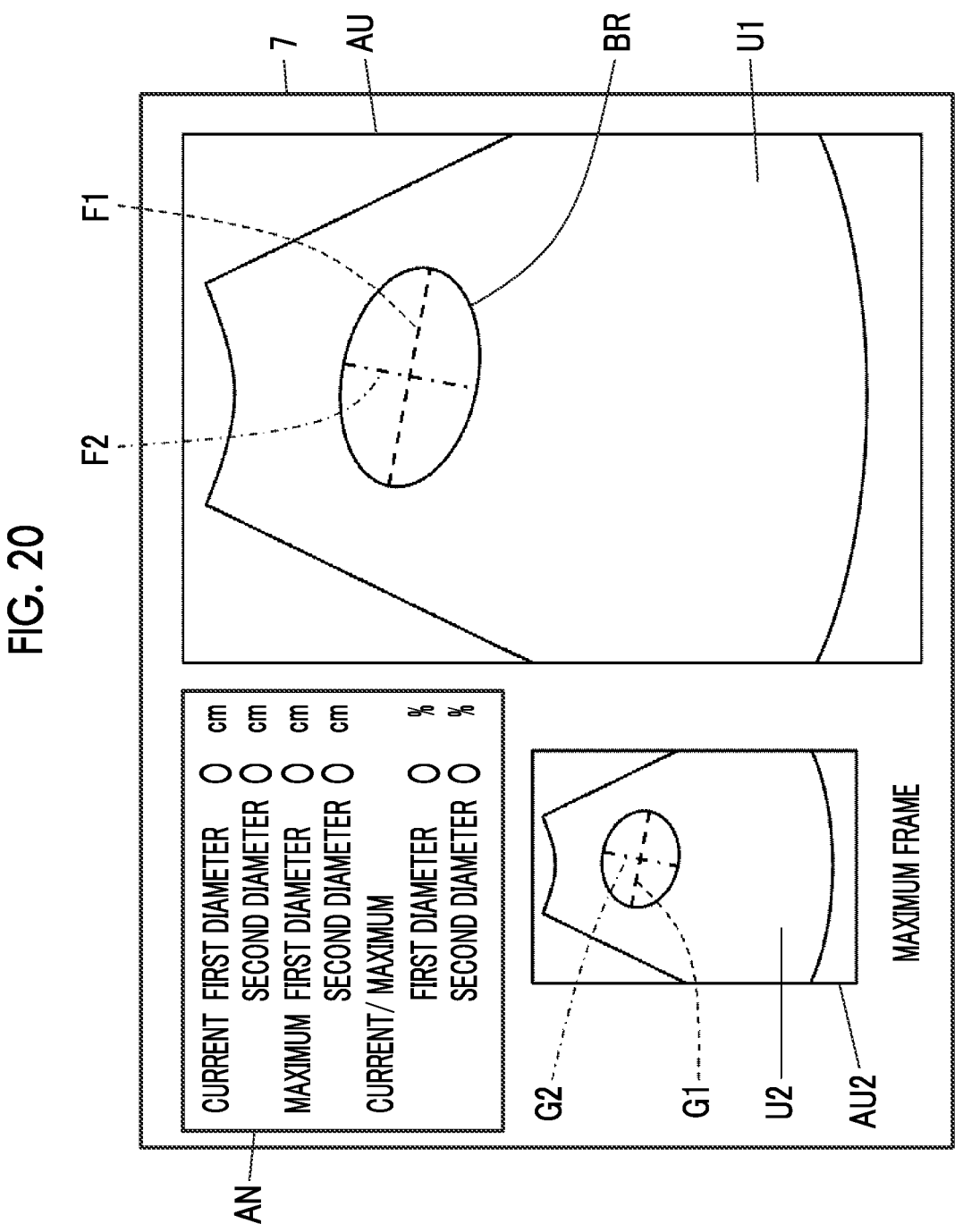
FIG. 20 is a diagram schematically illustrating an example in which an ultrasound image indicating the first maximum diameter and the second maximum diameter is displayed as the assist information on the monitor in the first embodiment of the present invention.

As illustrated in FIG. 20, the manipulation assist unit 11 can display an ultrasound image U2 indicating the first maximum diameter G1 and the second maximum diameter G2, as the assist information, on the monitor 7. In this case, the manipulation assist unit 11 can select the ultrasound image U2 with reference to the image memory 12, for example, and display the selected ultrasound image U2 on the monitor 7. In the example illustrated in FIG. 20, the monitor 7 has a maximum frame display region AU2 in addition to the current frame display region AU1 and the measurement value display region AN, and the ultrasound image U2 indicating the first maximum diameter G1 and the second maximum diameter G2 is displayed in the maximum frame display region AU2.

In this manner, in a case where the ultrasound image U2 indicating the first maximum diameter G1 and the second maximum diameter G2 is further displayed as the assist information on the monitor 7, the user can easily place the ultrasound probe 21 at the target slide position where the ultrasound image U1 indicating the first maximum diameter G1 and the second maximum diameter G2 is drawn, by comparing the ultrasound image U1 displayed in the current frame display region AU1 and the ultrasound image U2 displayed in the maximum frame display region AU2.

The manipulation assist unit 11 can display, for example, a difference between the first maximum diameter G1 and the current first diameter F1 and a difference between the second maximum diameter G2 and the current second diameter F2 as the assist information on the monitor 7 instead of displaying the ratio R1 of the current first diameter F1 to the first maximum diameter G1 and the ratio R2 of the current second diameter F2 to the second maximum diameter G2 as the assist information on the monitor 7. Here, the manipulation assist unit 11 can simply calculate a difference (G1– F1) between the value of the first maximum diameter G1 and the value of the current first diameter F1 and a difference (G2–F2) between the value of the second maximum diameter G2 and the value of the current second diameter F2 as the difference between the first maximum diameter G1 and the current first diameter F1 and the difference between the second maximum diameter G2 and the current second diameter F2. Further, the manipulation assist unit 11 can calculate a change rate (G1–F1)/G1 of the value of the current first diameter F1 to the value of the first maximum diameter G1 and a change rate (G2–F2)/G2 of the value of the current second diameter F2 to the value of the second maximum diameter G2 as the difference between the first maximum diameter G1 and the current first diameter F1 and the difference between the second maximum diameter G2 and the current second diameter F2. The change rate can be calculated as a percentage.

In this manner, in a case where the difference between the first maximum diameter G1 and the current first diameter F1 and the difference between the second maximum diameter G2 and the current second diameter F2 are calculated, the manipulation assist unit 11 can display the fact that the scanning section of the ultrasound probe 21 is the section indicating the first maximum diameter G1 and the second maximum diameter G2, on the monitor 7 in a case where both the difference between the first maximum diameter G1 and the current first diameter F1 and the difference between the second maximum diameter G2 and the current second diameter F2 are equal to or less than a difference threshold value.

The first diameter F1 and the second diameter F2 of the bladder region BR are illustrated as the feature quantity calculated by the feature quantity calculation unit 9, but the feature quantity is not limited thereto. For example, the feature quantity calculation unit 9 can calculate the product of the first diameter F1 and the second diameter F2 of the bladder region BR as the feature quantity. In this case, the first measurement unit 10 can select the ultrasound image U1 of the frame in which the product of the first diameter F1 and the second diameter F2 of the bladder region BR calculated for the ultrasound images U1 of the plurality of frames within the predetermined scanning time is maximum, and calculate the first maximum diameter G1 and the second maximum diameter G2 of the bladder region BR in the selected ultrasound image U1.

In this case, the manipulation assist unit 11 can display the product of the first diameter F1 and the second diameter F2 of the current bladder region BR, the product of the first maximum diameter G1 and the second maximum diameter G2, and a ratio of the product of the first diameter F1 and the second diameter F2 of the current bladder region BR to the product of the first maximum diameter G1 and the second maximum diameter G2, as the assist information on the monitor 7. The manipulation assist unit 11 can display a difference between the product of the first maximum diameter G1 and the second maximum diameter G2 and the product of the first diameter F1 and the second diameter F2 of the current bladder region BR as the assist information on the monitor 7 instead of the ratio of the product of the first diameter F1 and the second diameter F2 of the current bladder region BR to the product of the first maximum diameter G1 and the second maximum diameter G2.

Further, in a case where the ratio of the product of the first diameter F1 and the second diameter F2 of the current bladder region BR to the product of the first maximum diameter G1 and the second maximum diameter G2 exceeds the ratio threshold value, or in a case where the difference between the product of the first maximum diameter G1 and the second maximum diameter G2 and the product of the first diameter F1 and the second diameter F2 of the current bladder region BR is equal to or less than the difference threshold value, the manipulation assist unit 11 can display the fact that the scanning section of the ultrasound probe 21 is the section indicating the first maximum diameter G1 and the second maximum diameter G2, on the monitor 7.

For example, the feature quantity calculation unit 9 can calculate the area of the bladder region BR as the feature quantity. In this case, the first measurement unit 10 can select the ultrasound image U1 of the frame in which the area of the bladder region BR calculated for the ultrasound images U1 of the plurality of frames within the predetermined scanning time is maximum, and calculate the first maximum diameter G1 and the second maximum diameter G2 of the bladder region BR in the selected ultrasound image U1.

Figure 22:
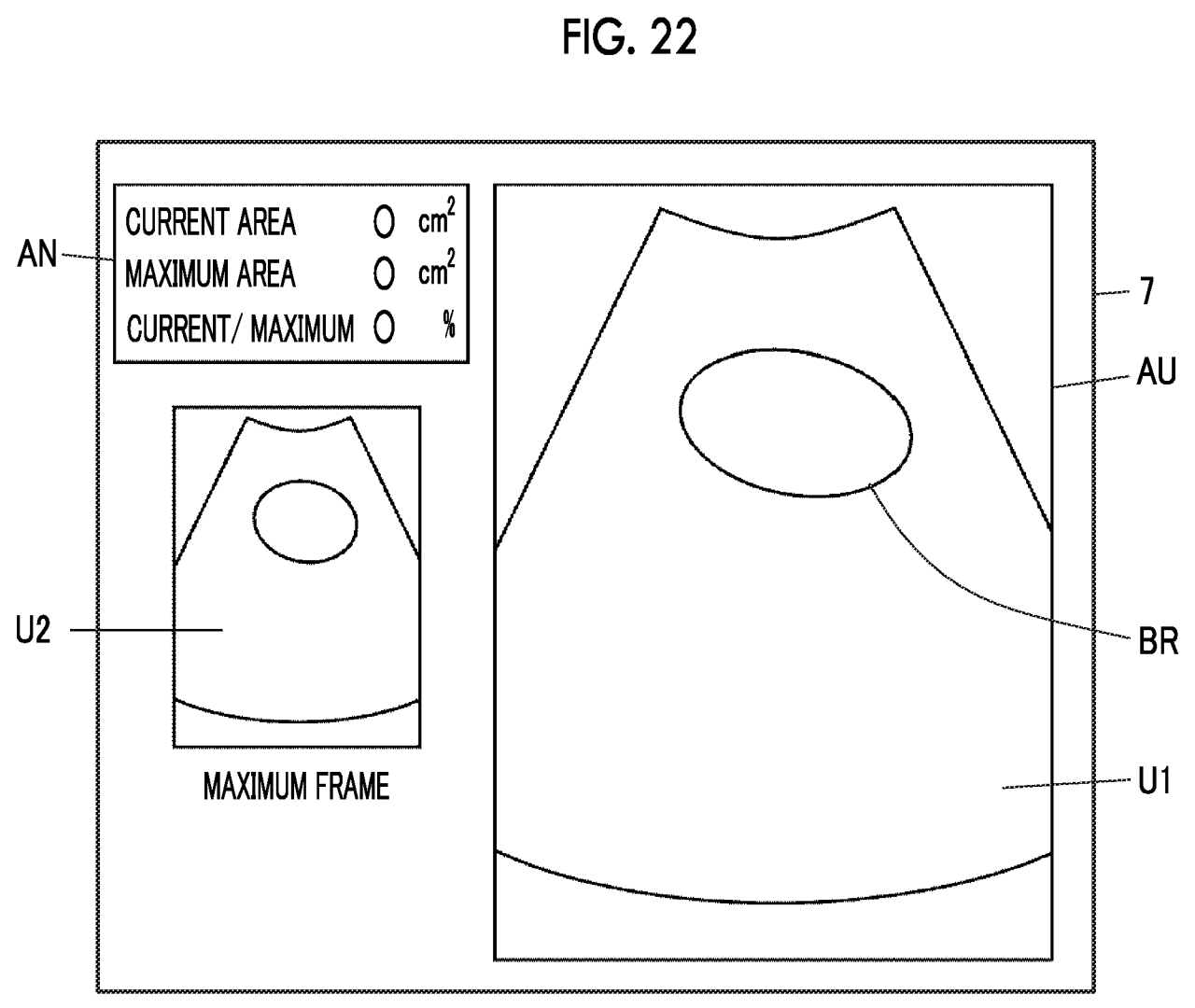

As illustrated in FIG. 21, the manipulation assist unit 11 can display the area of the bladder region BR in the ultrasound image U1 of the current frame, the maximum area of the bladder region BR in the ultrasound image U1 indicating the first maximum diameter G1 and the second maximum diameter G2, and a ratio of the area of the current bladder region BR to the maximum area, as the assist information on the monitor 7. In the example illustrated in FIG. 21, in the measurement value display region AN, values of the area of the current bladder region BR, the maximum area of the bladder region BR, and the ratio of the area of the current bladder region BR to the maximum area of the bladder region BR are displayed. The manipulation assist unit 11 can display the difference between the maximum area of the bladder region BR and the area of the current bladder region BR as the assist information on the monitor 7 instead of displaying the ratio of the area of the current bladder region BR to the maximum area of the bladder region BR on the monitor 7. Further, as illustrated in FIG. 22, the manipulation assist unit 11 can display the ultrasound image U2 indicating the maximum area of the bladder region BR, that is, the ultrasound image U2 indicating the first maximum diameter G1 and the second maximum diameter G2 on the monitor 7.

In a case where the ratio of the area of the current bladder region BR to the maximum area of the bladder region BR exceeds the ratio threshold value, or in a case were the difference between the maximum area of the bladder region BR and the area of the current bladder region BR is equal to or less than the difference threshold value, the manipulation assist unit 11 can display the fact that the scanning section of the ultrasound probe 21 is the section indicating the first maximum diameter G1 and the second maximum diameter G2, on the monitor 7.

In this manner, in a case where the ratio of the feature quantity to the maximum feature quantity exceeds the ratio threshold value, or in a case where the difference between the maximum feature quantity and the feature quantity is equal to or less than the difference threshold value, the manipulation assist unit 11 displays the fact that the scanning section of the ultrasound probe 21 is the section indicating the first maximum diameter G1 and the second maximum diameter G2 on the monitor 7, and therefore, the user can easily place the ultrasound probe 21 at the target slide position by checking the display.

Figure 23:
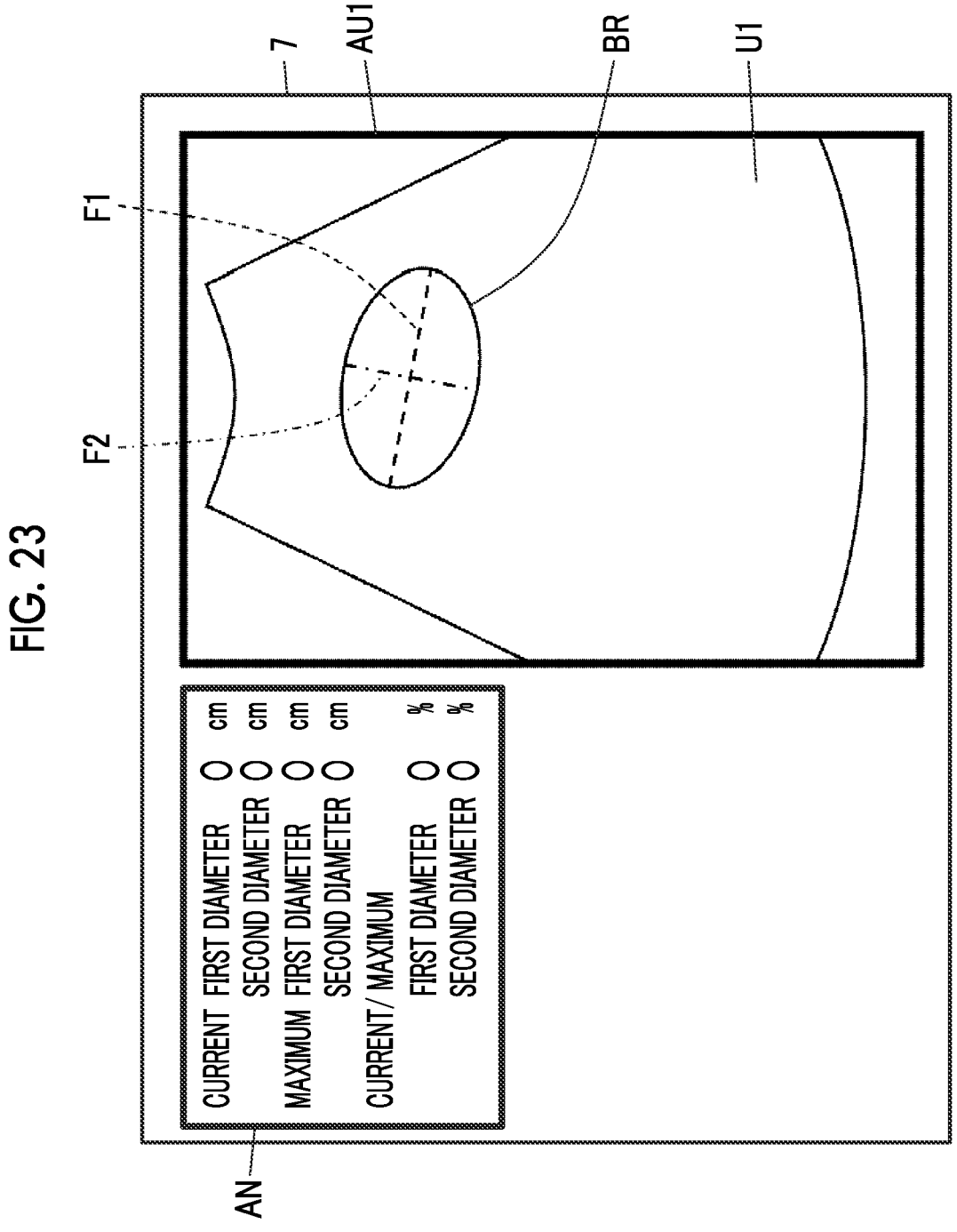
FIG. 23 is a diagram schematically illustrating an example in which frame lines of an ultrasound image display region and a measurement value display region are highlighted in the first embodiment of the present invention.

As the example of displaying the fact that the scanning section of the ultrasound probe 21 is the section indicating the first maximum diameter G1 and the second maximum diameter G2 on the monitor 7, the message M1 is displayed on the monitor 7 as illustrated in FIG. 6, but the invention is not limited thereto. For example, the manipulation assist unit 11 can represent the fact that the scanning section of the ultrasound probe 21 is the section indicating the first maximum diameter G1 and the second maximum diameter G2 by changing the display mode of the frame lines of the current frame display region AU1 and the measurement value display region AN as illustrated in FIG. 23. Here, changing the display mode of the frame line includes changing the color of the frame line, changing the thickness of the frame line, changing the frame line configured by a solid line to the frame line configured by a different line in the form of a broken line or the like.

Without being limited to changing the display mode of the frame lines of the current frame display region AU1 and the measurement value display region AN, for example, changing the display mode of the frame line of the monitor 7, changing the display mode of the value of the current feature quantity, changing the display mode of the ratio of the current feature quantity to the maximum feature quantity or the difference between the maximum feature quantity and the current feature quantity, changing the display mode of the bladder region BR in the ultrasound image U1 of the current frame, and the like can be performed.

It has been described that one ratio threshold value corresponding to the ratio of the current feature quantity to the maximum feature quantity or one difference threshold value corresponding to the difference between the maximum feature quantity and the current feature quantity is set, but a plurality of ratio threshold values corresponding to the ratio of the current feature quantity to the maximum feature quantity or a plurality of difference threshold values corresponding to the difference between the maximum feature quantity and the current feature quantity can be set. For example, in a case where a first ratio threshold value and a second ratio threshold value greater than the first ratio threshold value are set corresponding to the ratio of the current feature quantity to the maximum feature quantity, the manipulation assist unit 11 can display the assist information on the monitor 7 in each of a case where the ratio of the current feature quantity to the maximum feature quantity exceeds the first ratio threshold value and a case where the ratio of the current feature quantity to the maximum feature quantity exceeds the second ratio threshold value.

More specifically, for example, the frame line of the current frame display region AU1 and the frame line of the measurement value display region AN are displayed in black in a case where the ratio of the current feature quantity to the maximum feature quantity is equal to or less than the first ratio threshold value, and the manipulation assist unit 11 can display the frame line of the current frame display region AU1 and the frame line of the measurement value display region AN in blue in a case where the ratio of the current feature quantity to the maximum feature quantity exceeds the first ratio threshold value, and display the frame line of the current frame display region AU1 and the frame line of the measurement value display region AN in red in a case where the ratio of the current feature quantity to the maximum feature quantity exceeds the second ratio threshold value.

In this manner, since the manipulation assist unit 11 displays the assist information on the monitor 7 in stages according to the value of the ratio of the current feature quantity to the maximum feature quantity or the ratio of the difference between the maximum feature quantity and the current feature quantity, the user can easily grasp the relationship between the current slide position of the ultrasound probe 21 and the target slide position where the ultrasound image U1 indicating the first maximum diameter G1 and the second maximum diameter G2 is acquired, and thereby the user can easily place the ultrasound probe 21 at the target slide position.

Further, it has been described that, with reference to the scanning section PS1 in which the inclination angle A of the ultrasound probe 21 is zero, the second measurement unit 14 calculates the third direction length W1 that is maximum in a case where the ultrasound probe 21 is inclined in the positive direction, and the third direction length W2 that is maximum in a case where the ultrasound probe 21 is inclined in the negative direction, and calculates the sum of the third direction length W1 and the third direction length W2 to calculate the third maximum diameter H, but the third maximum diameter H can be calculated using any one of the third direction length W1 or the third direction length W2. For example, the second measurement unit 14 can consider that the target slide position assisted by the manipulation assist unit 11 is directly above the center of the bladder of the subject S, and calculate a value twice the third direction length W1 or the third direction length W2 as the value of the third maximum diameter H.

In this case, the user can obtain the third maximum diameter H by inclining the ultrasound probe 21 only in one side of the scanning section PS1, that is, in the positive direction or the negative direction with reference to the scanning section PS1. Therefore, the user can more easily measure the urine amount J in the bladder of the subject S.

The second measurement unit 14 calculates the third direction length W by the relational expression of W=L× |sin(A)| using the distance L from the body surface of the subject S to the deepest portion of the bladder region BR and the inclination angle A of the ultrasound probe 21, and calculates the third maximum diameter H of the bladder region BR on the basis of the calculated third direction length W, but the method of calculating the third maximum diameter H of the bladder region BR is not limited thereto.

Figure 24:
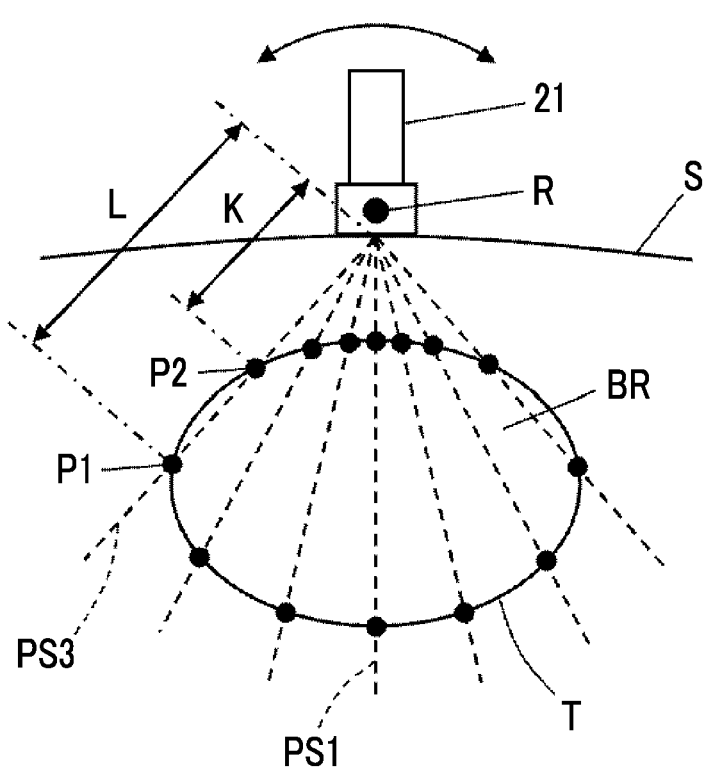
FIG. 24 is a diagram schematically illustrating a plurality of points positioned on a contour of a tomographic plane of the bladder of the subject in the first embodiment of the present invention.

For example, as illustrated in FIG. 24, the second measurement unit 14 can calculate the distance L from the body surface of the subject S to a deepest portion P1 of the bladder region BR and a distance K from the body surface of the subject S to a shallowest portion P2 for the ultrasound image U1 corresponding to each scanning section PS3 while the ultrasound probe 21 is inclined around the rotation axis R by the user, and acquire a contour T of the bladder region BR in the scanning section orthogonal to the rotation axis R on the basis of the distance L from the body surface of the subject S to the deepest portion P1 of the bladder region BR, the distance K from the body surface of the subject S to the shallowest portion P2 of the bladder region BR, and the inclination angle A of the ultrasound probe 21 that are calculated for the ultrasound images U1 of the plurality of frames. The second measurement unit 14 can calculate the maximum diameter of the contour T of the bladder region BR in a direction orthogonal to the scanning section PS1 in a state where the inclination angle A of the ultrasound probe 21 is zero, as the third maximum diameter H. For example, the second measurement unit 14 can calculate the shortest distance from the upper end portion of the ultrasound image U1 to the shallowest portion P2 of the bladder region BR in the direction along the scan line, as the distance K from the body surface of the subject S to the shallowest portion P2 of the bladder region BR.

The second measurement unit 14 can construct a three-dimensional model of the bladder region BR on the basis of the bladder region BR extracted by the bladder extraction unit 8 for the ultrasound images U1 of the plurality of frames acquired while the ultrasound probe 21 is inclined around the rotation axis R by the user, and calculate the third maximum diameter H of the bladder region BR on the basis of the constructed three-dimensional model of the bladder region BR.

It has been described that the manipulation assist unit 11 displays the fact that the scanning section of the ultrasound probe 21 is the section indicating the first maximum diameter G1 and the second maximum diameter G2 on the monitor 7, but the method of notifying the user that the scanning section of the ultrasound probe 21 is the section indicating the first maximum diameter G1 and the second maximum diameter G2 is not limited thereto.

Figure 25:
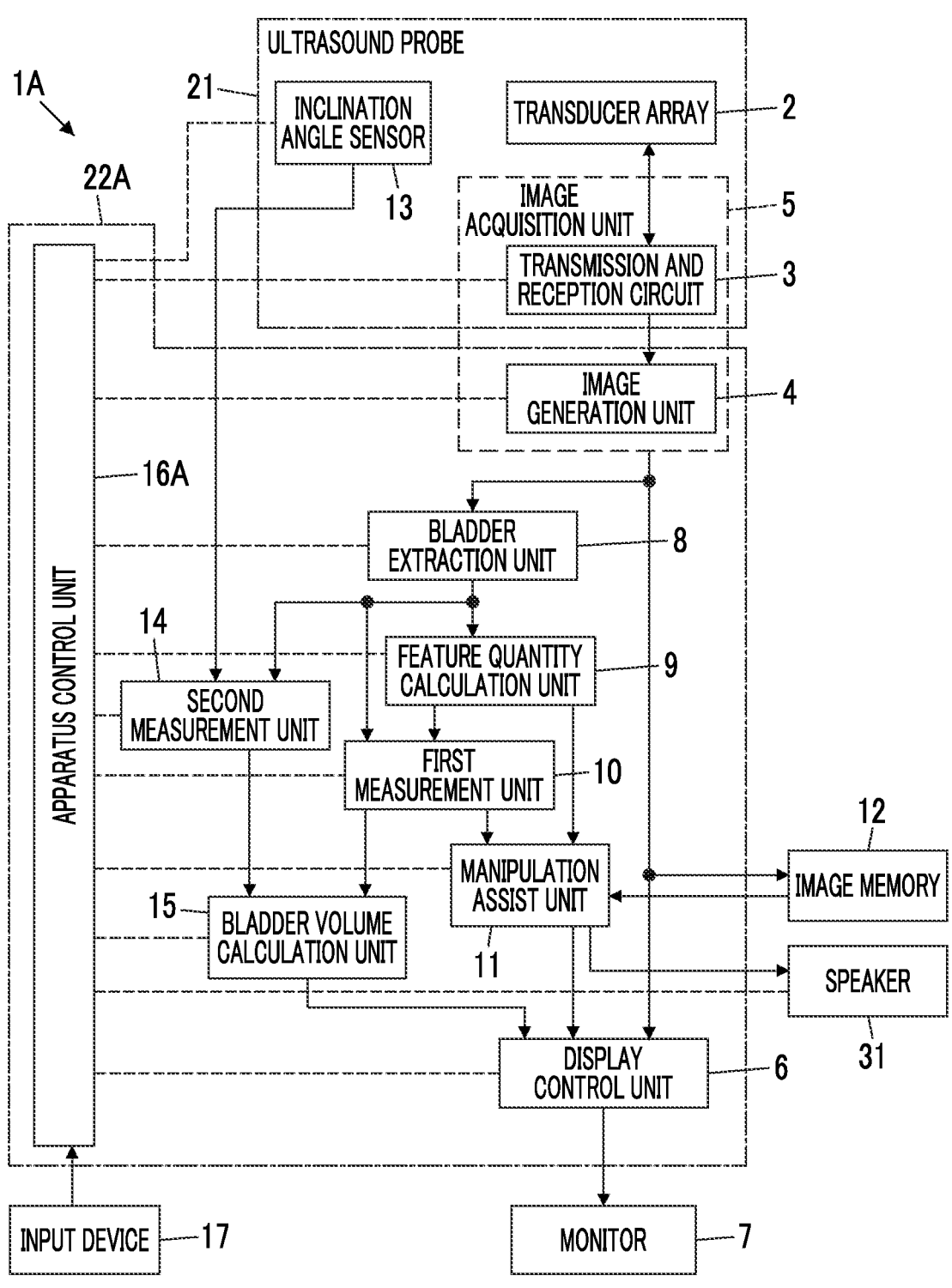
FIG. 25 is a block diagram illustrating a configuration of an ultrasound diagnostic apparatus according to a first modification example of the first embodiment of the present invention.

For example, the manipulation assist unit 11 can notify the user by a sound emitted from a speaker. FIG. 25 illustrates a configuration of an ultrasound diagnostic apparatus 1A according to a first modification example of the first embodiment. The ultrasound diagnostic apparatus 1A is obtained by adding a speaker 31, comprising an apparatus control unit 16A instead of the apparatus control unit 16, and comprising a processor 22A instead of the processor 22 in the ultrasound diagnostic apparatus 1 illustrated in FIG. 1. The speaker 31 is connected to the manipulation assist unit 11 and the apparatus control unit 16A.

In a case where the ratio of the feature quantity to the maximum feature quantity exceeds the ratio threshold value, or in a case where the difference between the maximum feature quantity and the feature quantity is equal to or less than the difference threshold value, the manipulation assist unit 11 can assist the user in the slide manipulation of the ultrasound probe 21 to the target slide position by notifying the user that the scanning section of the ultrasound probe 21 is the section indicating the first maximum diameter G1 and the second maximum diameter G2 by emitting the sound from the speaker 31.

Figure 26:
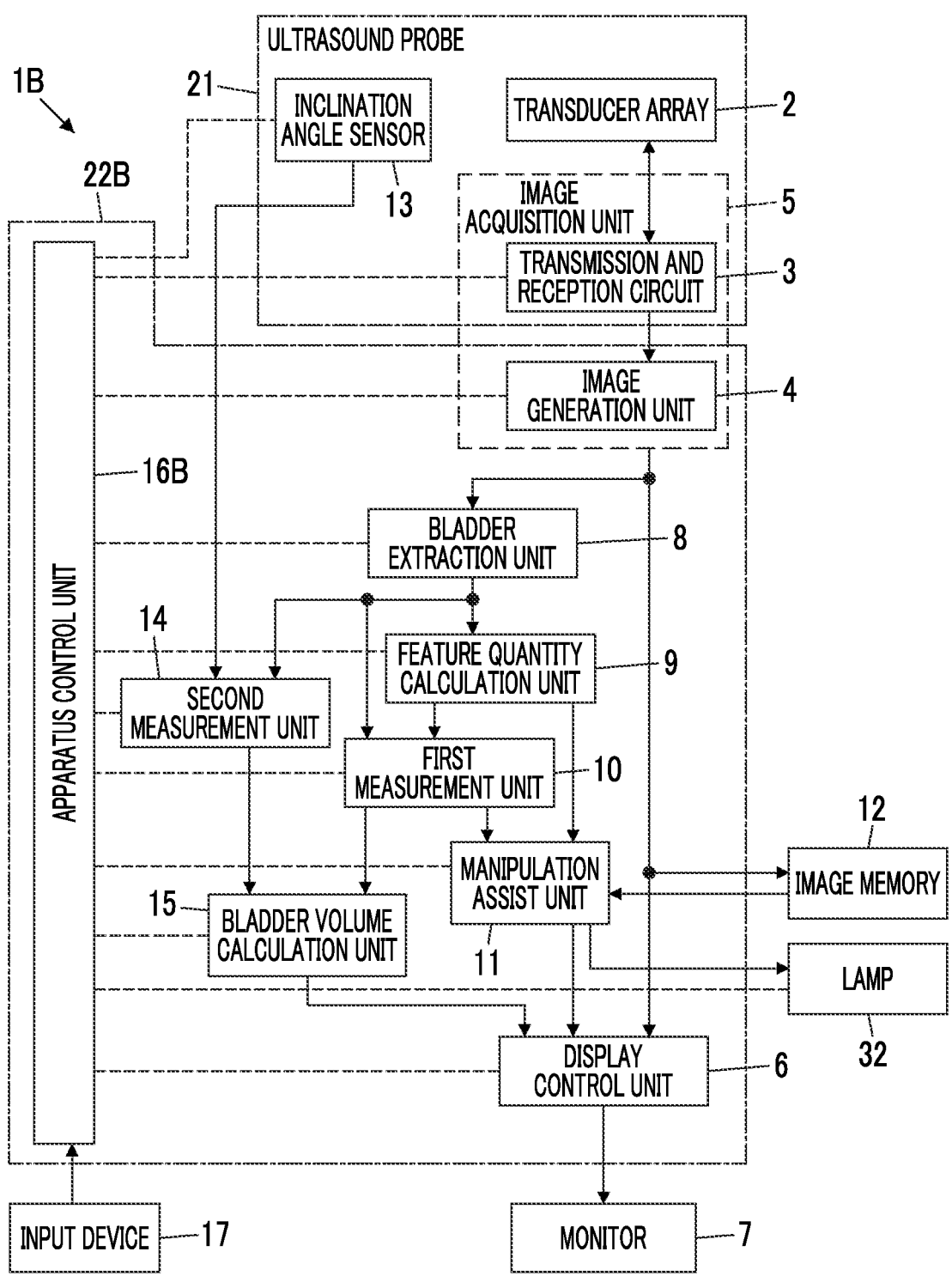
FIG. 26 is a block diagram illustrating a configuration of an ultrasound diagnostic apparatus according to a second modification example of the first embodiment of the present invention.

For example, the manipulation assist unit 11 can notify the user by light emitted from a lamp. FIG. 26 illustrates a configuration of an ultrasound diagnostic apparatus 1B according to a second modification example of the first embodiment. The ultrasound diagnostic apparatus 1B is obtained by adding a lamp 32, comprising an apparatus control unit 16B instead of the apparatus control unit 16, and comprising a processor 22B instead of the processor 22 in the ultrasound diagnostic apparatus 1 illustrated in FIG. 1. The lamp 32 is connected to the manipulation assist unit 11 and the apparatus control unit 16B.

In a case where the ratio of the feature quantity to the maximum feature quantity exceeds the ratio threshold value, or in a case where the difference between the maximum feature quantity and the feature quantity is equal to or less than the difference threshold value, the manipulation assist unit 11 can assist the user in the slide manipulation of the ultrasound probe 21 to the target slide position by notifying the user that the scanning section of the ultrasound probe 21 is the section indicating the first maximum diameter G1 and the second maximum diameter G2 by emitting the light from the lamp 32.

In a case where a user with a low skill level performs the inclination manipulation of the ultrasound probe 21, even when the ultrasound probe 21 is placed at the target slide position assisted by the manipulation assist unit 11, the slide position of the ultrasound probe 21 may be shifted from the target slide position assisted by the manipulation assist unit 11 due to the slipping of the ultrasound probe 21 on the body surface of the subject S while the ultrasound probe 21 is being inclined.

For example, in a case where the feature quantity in a state where the inclination angle A of the ultrasound probe 21 detected by the inclination angle sensor 13 is zero is equal to or less than a predetermined ratio to the feature quantity in a state where the ultrasound probe 21 is at the target slide position assisted by the manipulation assist unit 11 and the inclination angle A thereof is zero, the manipulation assist unit 11 can assist the user in the slide manipulation of the ultrasound probe 21 again. Thereby, even in a case where a user with a low skill level performs the inclination manipulation of the ultrasound probe 21, the inclination manipulation of the ultrasound probe 21 can be performed while placing the ultrasound probe 21 near a portion directly above the bladder of the subject S, and the urine amount J can be measured with high accuracy.

Here, in general, in a case where the ultrasound image is analyzed and the tissue in the subject S is extracted, the tissue as an extraction target may not be extracted normally because the tissue as the extraction target is not clearly drawn in the ultrasound image. Therefore, for example, in a case where the ultrasound image U1 is acquired while the slide manipulation of the ultrasound probe 21 is performed by the user on the body surface of the subject S within the predetermined scanning time, the bladder region BR in the ultrasound image U1 may not be normally extracted by the bladder extraction unit 8. In such a case, it is expected that the feature quantity of the bladder region BR calculated by the feature quantity calculation unit 9 for the bladder region BR that is not normally extracted is very small or very large compared to the feature quantity of the bladder region BR that is normally extracted.

In a case where the difference between feature quantities of the ultrasound images U1 of consecutive frames is greater than a predetermined value, the first measurement unit 10 can exclude the consecutive frames, and measure the first maximum diameter G1 and the second maximum diameter G2 on the basis of the feature quantities of the ultrasound images U1 of the other plurality of frames. Among the feature quantities calculated for the ultrasound images U1 of the plurality of frames by the feature quantity calculation unit 9, the first measurement unit 10 can exclude the feature quantity of which both the difference with the feature quantity in the ultrasound image U1 of the previous frame consecutive in time series and the difference with the feature quantity in the ultrasound image U1 of the subsequent frame consecutive in time series are greater than the predetermined value, and measure the first maximum diameter G1 and the second maximum diameter G2 on the basis of the other feature quantities. In this manner, the urine amount J can be measured with higher accuracy.

In the processing of Step S6, Step S24 of acquiring the inclination angle A of the ultrasound probe 21 is performed after Step S23 of calculating the distance L from the body surface of the subject S to the deepest portion P1 of the bladder region BR is completed, but Step S24 can be performed immediately before Step S21, immediately before Step S22, or immediately before Step S23 in the loop of Step S21 to Step S26.

The inclination angle sensor 13 can always detect the inclination angle A of the ultrasound probe 21, but can be controlled by the apparatus control unit 16 so as to be operated only in a case where the second measurement unit 14 measures the third maximum diameter H of the bladder region BR. In this manner, the apparatus control unit 16 controls the inclination angle sensor 13 such that the inclination angle sensor 13 is operated only in a case where the second measurement unit 14 measures the third maximum diameter H of the bladder region BR, and thereby the power consumption in the ultrasound diagnostic apparatus 1 can be reduced.

Second Embodiment

In the first embodiment, the apparatus main body (not illustrated) having the processor 22 and the ultrasound probe 21 are connected to each other by wired communication, but the apparatus main body and the ultrasound probe 21 can be connected by so-called wireless communication.

Figure 27:
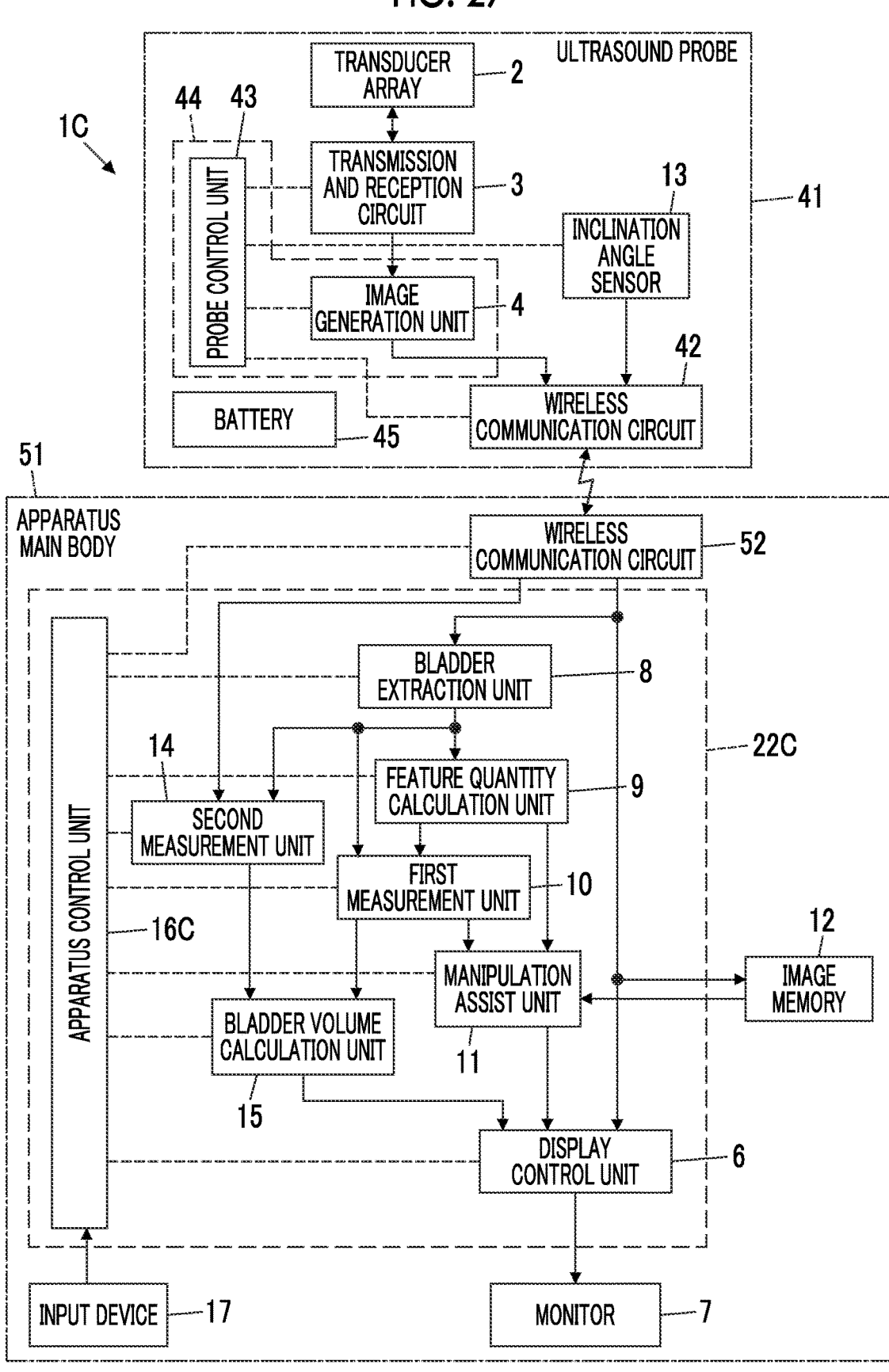
FIG. 27 is a block diagram illustrating a configuration of an ultrasound diagnostic apparatus according to a second embodiment of the present invention.

FIG. 27 illustrates a configuration of an ultrasound diagnostic apparatus 1C according to a second embodiment of the present invention. The ultrasound diagnostic apparatus 1C comprises an ultrasound probe 41 and an apparatus main body 51 that are connected to each other by wireless communication.

The ultrasound probe 41 is obtained by adding the image generation unit 4, a wireless communication circuit 42, a probe control unit 43, and a battery 45 in the ultrasound probe 21 in the first embodiment illustrated in FIG. 1. Here, the image generation unit 4 in the ultrasound probe 41 is the same as the image generation unit 4 in the first embodiment. In the ultrasound probe 41, the transmission and reception circuit 3 is connected to the transducer array 2, and the image generation unit 4 is connected to the transmission and reception circuit 3. Further, the wireless communication circuit 42 is connected to the image generation unit 4. The wireless communication circuit 42 is connected to the apparatus main body 51 by wireless communication. The probe control unit 43 is connected to the transmission and reception circuit 3, the image generation unit 4, the inclination angle sensor 13, and the wireless communication circuit 42. Further, the image generation unit 4 and the probe control unit 43 constitute a probe-side processor 44. The battery 45 is built in the ultrasound probe 41.

The apparatus main body 51 is obtained by excluding the ultrasound probe 21 including the transducer array 2, the transmission and reception circuit 3, and the inclination angle sensor 13, and the image generation unit 4, comprising an main body control unit 16C instead of the apparatus control unit 16, and adding a wireless communication circuit 52 in the ultrasound diagnostic apparatus 1 of the first embodiment illustrated in FIG. 1. The wireless communication circuit 52 of the apparatus main body 51 is connected to the ultrasound probe 41 by wireless communication. The display control unit 6, the bladder extraction unit 8, the second measurement unit 14, and the main body control unit 16C are connected to the wireless communication circuit 52. The display control unit 6, the bladder extraction unit 8, the feature quantity calculation unit 9, the first measurement unit 10, the manipulation assist unit 11, the second measurement unit 14, the bladder volume calculation unit 15, and the main body control unit 16C constitute a main body-side processor 22C. Although not illustrated, the transmission and reception circuit 3 and the image generation unit 4 constitute the image acquisition unit 5.

The image generation unit 4 of the ultrasound probe 41 generates the ultrasound image U1 by performing, on the sound ray signal generated by the beam former 26 of the transmission and reception circuit 3, correction of the attenuation, envelope detection processing, raster conversion, gradation processing, and the like according to the depth of the reflection position of the ultrasonic wave. The image generation unit 4 sends the generated ultrasound image U1 to the wireless communication circuit 42.

The inclination angle sensor 13 detects the inclination angle A of the ultrasound probe 41, and sends information representing the detected inclination angle A to the wireless communication circuit 42.

The wireless communication circuit 42 of the ultrasound probe 41 includes an antenna for transmitting and receiving radio waves, modulates a carrier on the basis of the ultrasound image U1 generated by the image generation unit 4, the information representing the inclination angle A of the ultrasound probe 41 detected by the inclination angle sensor 13, and the like, and generates a transmission signal representing the ultrasound image U1, the inclination angle A of the ultrasound probe 41, and the like, under the control of the probe control unit 43. The wireless communication circuit 42 transmits radio waves from the antenna by supplying the transmission signals generated in this manner to the antenna, and sequentially and wirelessly transmits the ultrasound image U1, the information representing the inclination angle A of the ultrasound probe 41, and the like to the wireless communication circuit 52 of the apparatus main body 51. As the modulation method of the carrier, amplitude shift keying (ASK), phase shift keying (PSK), quadrature phase shift keying (QPSK), 16 quadrature amplitude modulation (16QAM), or the like is used.

The wireless communication between the wireless communication circuit 42 of the ultrasound probe 41 and the wireless communication circuit 52 of the apparatus main body 51 can be performed in accordance with communication standards for mobile communication such as 5th generation mobile communication system (5G) and 4th generation mobile communication system (4G), and communication standards for short-range wireless communication such as WiFi (registered trademark), Bluetooth (registered trademark), and ultra wideband (UWB) communication system.

The probe control unit 43 controls each unit of the ultrasound probe 41 on the basis of a control program for the ultrasound probe 41 and the like stored in advance.

The battery 45 supplies power to each circuit of the ultrasound probe 41.

The wireless communication circuit 52 of the apparatus main body 51 includes an antenna for transmitting and receiving radio waves, receives the transmission signal representing the ultrasound image U1, the inclination angle A of the ultrasound probe 41, and the like that are wirelessly transmitted by the wireless communication circuit 42 of the ultrasound probe 41 via the antenna, demodulates the received transmission signal, and outputs the ultrasound image U1, the information representing the inclination angle A of the ultrasound probe 41, and the like, under the control of the main body control unit 16C. The wireless communication circuit 52 sends the output ultrasound image U1 to the display control unit 6, the bladder extraction unit 8, and the second measurement unit 14, and sends the output inclination angle A of the ultrasound probe 41 to the second measurement unit 14.

The bladder extraction unit 8 extracts the bladder region BR from each of the ultrasound images U1 of the plurality of frames sequentially sent from the wireless communication circuit 52.

The feature quantity calculation unit 9 calculates the feature quantity of the bladder region BR extracted by the bladder extraction unit 8, in each of the ultrasound images U1 of the plurality of frames.

The first measurement unit 10 measures the first maximum diameter G1 and the second maximum diameter G2 of the bladder region BR on the basis of the feature quantity calculated by the feature quantity calculation unit 9 from the ultrasound image U1 generated by the image generation unit 4 while the ultrasound probe 41 is being slid along the body surface of the subject S by the user.

The manipulation assist unit 11 assists the user in a slide manipulation of the ultrasound probe 41 to the target slide position such that the scanning section of the ultrasound probe 41 is a section indicating the first maximum diameter G1 and the second maximum diameter G2. For example, the manipulation assist unit 11 can assist the user by displaying, on the monitor 7, the assist information such as the current ultrasound image U1, the first diameter F1 and the second diameter F2 of the current bladder region BR, the first maximum diameter G1, the second maximum diameter G2, the ratio R1 of the first diameter F1 of the current bladder region BR to the first maximum diameter G1, and the ratio R2 of the second diameter F2 of the current bladder region BR to the second maximum diameter G2, as illustrated in FIG. 5. Although not illustrated, the manipulation assist unit 11 can also display the difference between the first maximum diameter G1 and the first diameter F1 of the current bladder region BR and the difference between the second maximum diameter G2 and the second diameter F2 of the current bladder region BR as the assist information on the monitor 7.

Further, as illustrated in FIG. 6, in a case where both the ratio R1 of the current first diameter F1 to the first maximum diameter G1 and the ratio R2 of the current second diameter F2 to the second maximum diameter G2 exceed the ratio threshold value, or in a case where both the difference between the first maximum diameter G1 and the first diameter F1 of the current bladder region F1 and the difference between the second maximum diameter G2 and the second diameter F2 of the current bladder region are equal to or less than the difference threshold value, the manipulation assist unit 11 can display the message M1 representing that the scanning section of the ultrasound probe 41 is the section indicating the first maximum diameter G1 and the second maximum diameter G2, on the monitor 7.

In this manner, the manipulation assist unit 11 can display the feature quantity of the current bladder region BR, the maximum feature quantity of the bladder region BR, the ratio of the feature quantity of the current bladder region BR to the maximum feature quantity, the difference between the maximum feature quantity and the feature quantity of the current bladder region BR, and the like as the assist information on the monitor 7. Further, in a case where the ratio of the feature quantity of the current bladder region BR to the maximum feature quantity exceeds the ratio threshold value, or in a case where the difference between the maximum feature quantity and the feature quantity of the current bladder region BR is equal to or less than the difference threshold value, the manipulation assist unit 11 can notify the user that the scanning section of the ultrasound probe 41 is the section indicating the first maximum diameter G1 and the second maximum diameter G2.

The second measurement unit 14 measures the third maximum diameter H of the bladder region BR on the basis of the ultrasound image U1 generated by the image generation unit 4 and the inclination angle A of the ultrasound probe 41 while changing the inclination angle A of the ultrasound probe 41 at the target slide position assisted by the manipulation assist unit 11.

The bladder volume calculation unit 15 calculates the volume of the bladder as the urine amount J in the bladder of the subject S, on the basis of the first maximum diameter G1 and the second maximum diameter G2 measured by the first measurement unit 10 and the third maximum diameter H measured by the second measurement unit 14. Further, the bladder volume calculation unit 15 displays the calculated urine amount J on the monitor 7, as illustrated in FIG. 18, for example.

From the above, with the ultrasound diagnostic apparatus 1C according to the second embodiment of the present invention, even in a case where the ultrasound probe 41 and the apparatus main body 51 are connected to each other by wireless communication, similar to the ultrasound diagnostic apparatus 1 of the first embodiment, since the user is assisted in the slide manipulation of the ultrasound probe 41 to the target slide position such that the scanning section of the ultrasound probe 41 is a section indicating the first maximum diameter G1 and the second maximum diameter G2, it is suppressed that the ultrasound probe 41 is separated from the body surface of the subject S, and that the slide position of the ultrasound probe 41 is shifted when the user performs the inclination manipulation of the ultrasound probe 41 at the assisted target slide position, and thus the urine amount J in the bladder of the subject S can be measured with high accuracy.

Even in the ultrasound diagnostic apparatus 1C according to the second embodiment, similar to the ultrasound diagnostic apparatus 1 of the first embodiment, the inclination angle sensor 13 can always detect the inclination angle A of the ultrasound probe 41, but can be controlled by the probe control unit 43 such that the inclination angle sensor 13 is operated only in a case where the second measurement unit 14 of the apparatus main body 51 measures the third maximum diameter H of the bladder region BR.

In this case, for example, measurement start information representing that the measurement of the third maximum diameter H by the second measurement unit 14 is started is wirelessly transmitted from the main body control unit 16C of the apparatus main body 51 to the wireless communication circuit 42 of the ultrasound probe 41 via the wireless communication circuit 52 of the apparatus main body 51, the measurement start information is sent from the wireless communication circuit 42 to the probe control unit 43 of the ultrasound probe 41, and thereby the probe control unit 43 can start the operation of the inclination angle sensor 13. Further, for example, measurement end information representing that the measurement of the third maximum diameter H by the second measurement unit 14 is ended is wirelessly transmitted from the main body control unit 16C of the apparatus main body 51 to the wireless communication circuit 42 of the ultrasound probe 41 via the wireless communication circuit 52 of the apparatus main body 51, the measurement end information is sent from the wireless communication circuit 42 to the probe control unit 43 of the ultrasound probe 41, and thereby the probe control unit 43 can stop the inclination angle sensor 13.

In this manner, in the ultrasound diagnostic apparatus 1C in which the ultrasound probe 41 and the apparatus main body 51 are connected to each other by wireless communication, since the inclination angle sensor 13 is controlled by the probe control unit 43 such that the inclination angle sensor 13 is operated only in a case where the second measurement unit 14 of the apparatus main body 51 measures the third maximum diameter H of the bladder region BR, the power consumption in the ultrasound probe 41 can be reduced, and the consumption of the battery 45 can be suppressed.

Third Embodiment

In the ultrasound diagnostic apparatus 1 according to the first embodiment, the ultrasound probe 21, the monitor 7, and the input device 17 are connected to the apparatus main body (not illustrated) having the processor 22 by wired communication, but the ultrasound probe 21, the monitor 7, and the input device 17 can be connected to a network, for example.

Figure 28:
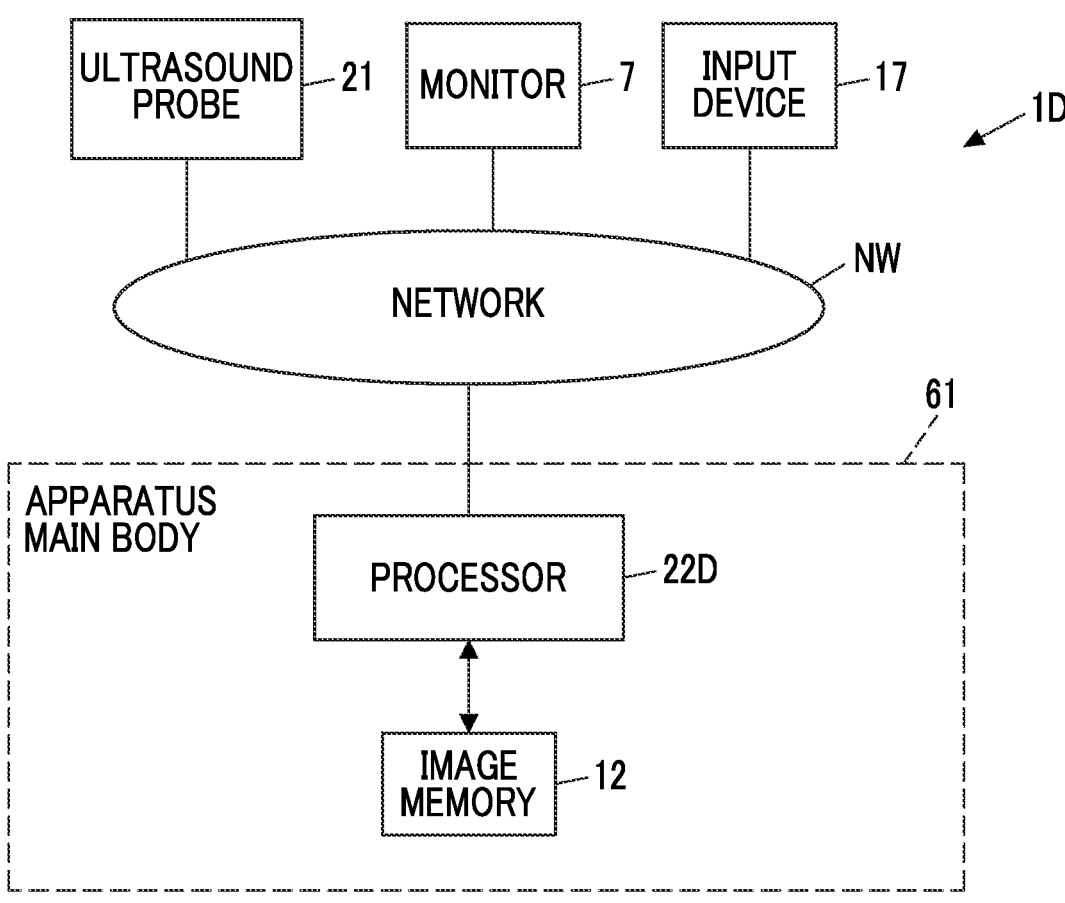
FIG. 28 is a block diagram illustrating a configuration of an ultrasound diagnostic apparatus according to a third embodiment of the present invention.

FIG. 28 illustrates a configuration of an ultrasound diagnostic apparatus 1D according to a third embodiment of the present invention. In the ultrasound diagnostic apparatus 1D according to the third embodiment, the ultrasound probe 21, the monitor 7, and the input device 17 are connected to an apparatus main body 61 via a network NW. The apparatus main body 61 is obtained by excluding the ultrasound probe

21, the monitor 7, and the input device 17 and comprising a processor 22D instead of the processor 22 in the ultrasound diagnostic apparatus 1 of the first embodiment illustrated in FIG. 1.

Here, in a state where the ultrasound probe 21 is pressed against the subject S by the user, in a case where the ultrasound beam is transmitted from the transducer array 2 of the ultrasound probe 21 toward the inside of the subject S, the ultrasound echo reflected inside the subject S is received by the transducer array 2 to generate the reception signal, and the sound ray signal is generated by the transmission and reception circuit 3 on the basis of the reception signal. The ultrasound probe 21 transmits the generated sound ray signal to the apparatus main body 61 via the network NW. The sound ray signal transmitted from the ultrasound probe 21 in this manner is input to the image generation unit 4 of the processor 22D of the apparatus main body 61 via the network NW, and the ultrasound image U1 is generated by the image generation unit 4 on the basis of the sound ray signal.

The bladder extraction unit 8 of the apparatus main body 61 extracts the bladder region BR from each of ultrasound images U1 of the plurality of frames generated by the image generation unit 4.

The feature quantity calculation unit 9 calculates the feature quantity of the bladder region BR extracted by the bladder extraction unit 8, in each of the ultrasound images U1 of the plurality of frames.

The first measurement unit 10 measures the first maximum diameter G1 and the second maximum diameter G2 of the bladder region BR on the basis of the feature quantity calculated by the feature quantity calculation unit 9 from the ultrasound image U1 generated by the image generation unit 4 while the ultrasound probe 21 is being slid along the body surface of the subject S by the user.

The manipulation assist unit 11 assists the user in a slide manipulation of the ultrasound probe 21 to the target slide position such that the scanning section of the ultrasound probe 21 is a section indicating the first maximum diameter G1 and the second maximum diameter G2. For example, the manipulation assist unit 11 can display the feature quantity of the current bladder region BR, the maximum feature quantity of the bladder region BR, the ratio of the feature quantity of the current bladder region BR to the maximum feature quantity, the difference between the maximum feature quantity and the feature quantity of the current bladder region BR, and the like as the assist information on the monitor 7. Further, in a case where the ratio of the feature quantity of the current bladder region BR to the maximum feature quantity exceeds the ratio threshold value, or in a case where the difference between the maximum feature quantity and the feature quantity of the current bladder region BR is equal to or less than the difference threshold value, the manipulation assist unit 11 can notify the user that the scanning section of the ultrasound probe 21 is the section indicating the first maximum diameter G1 and the second maximum diameter G2.

The second measurement unit 14 measures the third maximum diameter H of the bladder region BR on the basis of the ultrasound image U1 generated by the image generation unit 4 and the inclination angle A of the ultrasound probe 21 while changing the inclination angle A of the ultrasound probe 21 at the target slide position assisted by the manipulation assist unit 11.

The bladder volume calculation unit 15 calculates the volume of the bladder as the urine amount J in the bladder of the subject S, on the basis of the first maximum diameter G1 and the second maximum diameter G2 measured by the first measurement unit 10 and the third maximum diameter H measured by the second measurement unit 14. Further, the bladder volume calculation unit 15 displays the calculated urine amount J on the monitor 7, as illustrated in FIG. 18, for example.

From the above, with the ultrasound diagnostic apparatus 1D according to the third embodiment of the present invention, even in a case where the ultrasound probe 21, the monitor 7, the input device 17, and the apparatus main body 61 are connected to each other via the network NW, similar to the ultrasound diagnostic apparatus 1 of the first embodiment, since the user is assisted in the slide manipulation of the ultrasound probe 21 to the target slide position such that the scanning section of the ultrasound probe 21 is a section indicating the first maximum diameter G1 and the second maximum diameter G2, it is suppressed that the ultrasound probe 21 is separated from the body surface of the subject S, and that the slide position of the ultrasound probe 21 is shifted when the user performs the inclination manipulation of the ultrasound probe 21 at the assisted target slide position, and thus the urine amount J in the bladder of the subject S can be measured with high accuracy.

Further, since the ultrasound probe 21, the monitor 7, and the input device 17 are connected to the apparatus main body 61 via the network NW, the apparatus main body 61 can be used as a so-called remote server. Thereby, for example, since the user can perform the measurement of the urine amount for the subject S by preparing only the ultrasound probe 21, the monitor 7, and the input device 17 at the user's hand, it is possible to improve the convenience in a case of performing the measurement of the urine amount.

Further, in a case where a portable thin computer, for example, a so-called tablet, is used as the monitor 7 and the input device 17, it is possible for the user to more easily perform the measurement of the urine amount for the subject S, and it is possible to further improve the convenience in a case of performing the measurement of the urine amount.

The ultrasound probe 21 and the apparatus main body 61 are connected to each other via the network NW, but the ultrasound probe 21 and the apparatus main body 61 can be connected to the network NW by wired communication, or can be connected to the network NW by wireless communication as in the ultrasound diagnostic apparatus 1C of the second embodiment. Further, the monitor 7 and the input device 17 can be connected to the network NW by wired communication, or can be connected to the network NW by wireless communication.

EXPLANATION OF REFERENCES 1, 1A, 1B, 1C, 1D: ultrasound diagnostic apparatus
2: transducer array
3: transmission and reception circuit
4: image generation unit
5: image acquisition unit
6: display control unit
7: monitor
8: bladder extraction unit
9: feature quantity calculation unit
10: first measurement unit
11: manipulation assist unit
12: image memory
13: inclination angle sensor
14: second measurement unit
15: bladder volume calculation unit
16, 16A, 16B: apparatus control unit 16C: main body control unit
17: input device
21, 41: ultrasound probe
22, 22A, 22B, 22D: processor
22C: main body-side processor
23: puller
24: amplification unit
25: AD conversion unit
26: beam former
27: signal processing unit
28: DSC
29: image processing unit
31: speaker
32: lamp
42, 52: wireless communication circuit
43: probe control unit
44: probe-side processor
45: battery
51, 61: apparatus main body
A, A1, A2: inclination angle
AU1: current frame display region
AN: measurement value display region
BR: bladder region
C: center
D1: lateral direction
D2: vertical direction
E: ellipsoid
F1: first diameter
F2: second diameter
H: third maximum diameter
L, L1, L2, K: distance
LX, LY, LZ: maximum diameter
M1, M2: message
NW: network
P1: deepest portion
P2: shallowest portion
PP1: first contact position
PP2: second contact position
PS1, PS2, PS3: scanning section
R: rotation axis
RT: retry button
S: subject
T: contour
U1, U2: ultrasound image
W, W1, W2: third direction length
What is claimed is:

1. An ultrasound diagnostic apparatus comprising:
an ultrasound probe that is brought into contact with a subject and configured to perform scanning of an ultrasound beam on the subject;
an inclination angle sensor device configured to detect an inclination angle of the ultrasound probe;
a first processor configured to
acquire ultrasound images of a first plurality of frames based on a first sound ray signal generated while the ultrasound probe is being slid along a body surface of the subject,
extract a bladder region from each of the ultrasound images of the first plurality of frames,
calculate a feature quantity relating to the bladder region which is extracted in each of the ultrasound images of the first plurality of frames,
select an ultrasound image of a first measuring frame having a maximum feature quantity from the ultrasound images of the plurality of frames,
measure a first maximum diameter and a second maximum diameter of the bladder region in two directions in a scanning section of the ultrasound probe based on the ultrasound image of the first measuring frame, assist a user in a slide manipulation of the ultrasound probe to a target slide position along the body surface corresponding to the ultrasound image of the first measuring frame, acquire ultrasound images of a second plurality of frames based on a second sound ray signal generated while the ultrasound probe is being inclined at the target slide position, measure a distance between the body surface and a deepest position of the bladder region on each of the ultrasound images of the second plurality of frames, measure a third maximum diameter of the bladder region in a section orthogonal to the scanning section corresponding to the ultrasound image of the first measuring frame based on distances measured on the ultrasound images of the second plurality of frames and inclination angles of the ultrasound probe detected by the inclination angle sensor, and calculate a volume of the bladder based on the first maximum diameter and the second maximum diameter and the third maximum diameter.

2. The ultrasound diagnostic apparatus according to claim 1, wherein the first processor is further configured to calculate a first diameter and a second diameter of the bladder region in the two directions in the scanning section of the ultrasound probe, as the feature quantity.

3. The ultrasound diagnostic apparatus according to claim 1, wherein the first processor is further configured to calculate a product of a first diameter and a second diameter of the bladder region in the two directions in the scanning section of the ultrasound probe, as the feature quantity.

4. The ultrasound diagnostic apparatus according to claim 1, wherein the first processor is further configured to calculate an area of the bladder region in the scanning section of the ultrasound probe, as the feature quantity.

5. The ultrasound diagnostic apparatus according to claim 1, further comprising:

a monitor configured to display the ultrasound image, wherein the first processor is further configured to assist the user in the slide manipulation of the ultrasound probe to the target slide position by displaying assist information on the monitor.

6. The ultrasound diagnostic apparatus according to claim 5, wherein the first processor is further configured to display a ratio or difference between the feature quantity and the maximum feature quantity, as the assist information on the monitor.

7. The ultrasound diagnostic apparatus according to claim 6, wherein once the ratio of the feature quantity to the maximum feature quantity exceeds a ratio threshold value, or once the difference between the maximum feature quantity and the feature quantity is equal to or less than a difference threshold value, the first processor is further configured to display that the scanning section of the ultrasound probe is a section indicating the first maximum diameter and the second maximum diameter, on the monitor.

8. The ultrasound diagnostic apparatus according to claim 5, wherein the first processor is further configured to display the ultrasound image representing the scanning section indicating the first maximum diameter and the second maximum diameter, as the assist information on the monitor.

9. The ultrasound diagnostic apparatus according to claim 1, further comprising:

a speaker, wherein the first processor is further configured to assist the user in the slide manipulation of the ultrasound probe to the target slide position by emitting a sound from the speaker.

10. The ultrasound diagnostic apparatus according to claim 1, further comprising:

a lamp, wherein the first processor is configured to assist the user in the slide manipulation of the ultrasound probe to the target slide position by emitting light from the lamp.

11. The ultrasound diagnostic apparatus according to claim 1, wherein once the feature quantity calculated in a state where the inclination angle of the ultrasound probe detected by the inclination angle sensor device is zero is equal to or less than a predetermined ratio to the feature quantity calculated in a state where the ultrasound probe is placed at the target slide position and the inclination angle of the ultrasound probe detected by the inclination angle sensor device is zero, the first processor is further configured to assist the user in the slide manipulation of the ultrasound probe to the target slide position again.

12. The ultrasound diagnostic apparatus according to claim 1, wherein the first processor is further configured to measure the third maximum diameter based on the ultrasound image acquired while the inclination angle of the ultrasound probe is changed by inclining the ultrasound probe only in one side of the scanning section, and the inclination angle of the ultrasound probe.

13. The ultrasound diagnostic apparatus according to claim 1, wherein the first processor is further configured to control the inclination angle sensor device such that the inclination angle sensor device is operated only when the third maximum diameter is measured.

14. The ultrasound diagnostic apparatus according to claim 1, further comprising:

an apparatus main body that includes at least the first processor, and is connected to the ultrasound probe by wireless communication, wherein the ultrasound probe includes at least the inclination angle sensor device, and a second processor configured to control the inclination angle sensor device such that the inclination angle sensor device is operated only when the third maximum diameter is measured.

15. The ultrasound diagnostic apparatus according to claim 1, wherein the first processor is further configured to measure the first maximum diameter and the second maximum diameter based on the feature quantity calculated within a predetermined scanning time.

16. The ultrasound diagnostic apparatus according to claim 15, further comprising:

an input device configured to perform an input operation by the user, wherein once an instruction to measure again the first maximum diameter and the second maximum diameter is input by the user through the input device, the first processor is further configured to measure again the first maximum diameter and the second maximum diameter based on the feature quantity calculated in the predetermined scanning time.

17. The ultrasound diagnostic apparatus according to claim 16, wherein the scanning time is adjusted based on the user's input operation through the input device.

18. The ultrasound diagnostic apparatus according to claim 1, wherein once a difference between the feature quantities of the ultrasound images of the consecutive frames is greater than a predetermined value, the first processor is further configured to measure the first maximum diameter and the second maximum diameter based on the feature quantities of the ultrasound images of the frames other than the consecutive frames.

19. A control method of an ultrasound diagnostic apparatus, the control method comprising:

performing scanning of an ultrasound beam on a subject by an ultrasound probe in contact with the subject;

detecting an inclination angle of the ultrasound probe;

acquiring ultrasound images of a first plurality of frames in the subject based on a first sound ray signal generated while the ultrasound probe is being slid along a body surface of the subject;

extracting a bladder region from each of the ultrasound images of the first plurality of frames;

calculating a feature quantity relating to the bladder region which is extracted in each of the ultrasound images of the first plurality of frames;

selecting an ultrasound image of a first measuring frame having a maximum feature quantity from the ultrasound images of the plurality of frames;

measuring a first maximum diameter and a second maximum diameter of the bladder region in two directions in a scanning section of the ultrasound probe based on the ultrasound image of the first measuring frame;

assisting a user in a slide manipulation of the ultrasound probe to a target slide position along the body surface corresponding to the ultrasound image of the first measuring frame;

acquiring ultrasound images of a second plurality of frames based on a second sound ray signal generated while the ultrasound probe is being inclined at the target slide position;

measuring a distance between the body surface and a deepest position of the bladder region on each of the ultrasound images of the second plurality of frames;

measuring a third maximum diameter of the bladder region in a section orthogonal to the scanning section corresponding to the ultrasound image of the first measuring frame based on distances measured on the ultrasound images of the second plurality of frames and detected inclination angles of the ultrasound probe; and calculating a volume of the bladder based on the measured first maximum diameter and second maximum diameter and the measured third maximum diameter.

* * * * *